United States Patent
Akiyama et al.

Patent Number: 5,817,829
Date of Patent: Oct. 6, 1998

[54] PYRAZOLECARBOXYLIC ACID DERIVATIVES AND PLANT DISEASE CONTROL AGENT

[75] Inventors: Shigeaki Akiyama; Toshiaki Takeyama; Junichi Watanabe; Yasuyuki Nakajima; Hiroyuki Suzuki; Yoshiaki Yasumi; Takamasa Kikuchi, all of Funabashi; Hiroshi Ohya, Minamisaitama; Shigeru Sasabe, Minamisaitama; Masanori Nishioka, Minamisaitama; Takashi Furusato, Minamisaitama, all of Japan

[73] Assignee: Nissan Chemical Industries, Ltd., Tokyo, Japan

[21] Appl. No.: 727,571

[22] PCT Filed: Apr. 25, 1995

[86] PCT No.: PCT/JP95/00808

§ 371 Date: Oct. 23, 1996

§ 102(e) Date: Oct. 23, 1996

[87] PCT Pub. No.: WO95/29161

PCT Pub. Date: Nov. 2, 1995

[30] Foreign Application Priority Data

Apr. 27, 1994 [JP] Japan .................................... 6-089903
Apr. 17, 1995 [JP] Japan .................................... 7-091058

[51] Int. Cl.⁶ .......................... C07D 231/16; A01N 43/56
[52] U.S. Cl. ........................ 548/374.1; 544/238; 546/211; 546/275.4; 548/364.1; 548/364.4; 548/365.7; 548/375.1; 548/376.1; 514/406
[58] Field of Search .................. 548/374.1, 376.1, 548/375.1; 514/406

[56] References Cited

U.S. PATENT DOCUMENTS 3,700,657  10/1972  Nordin .

FOREIGN PATENT DOCUMENTS

| | | |
|---|---|---|
| A-005204 | 11/1979 | European Pat. Off. . |
| A-087780 | 9/1983 | European Pat. Off. . |
| A-276177 | 7/1988 | European Pat. Off. . |
| A-279239 | 8/1988 | European Pat. Off. . |
| A-333131 | 9/1989 | European Pat. Off. . |
| A-394043 | 10/1990 | European Pat. Off. . |
| A-463756 | 1/1992 | European Pat. Off. . |
| A-514217 | 11/1992 | European Pat. Off. . |
| A-571326 | 11/1993 | European Pat. Off. . |
| A-707000 | 4/1996 | European Pat. Off. . |
| A-2337997 | 8/1977 | France . |
| A-54-143521 | 11/1979 | Japan . |
| A-62-120369 | 6/1987 | Japan . |
| A-63-201178 | 8/1988 | Japan . |
| A-1-25763 | 1/1989 | Japan . |
| A-01-168-675 | 7/1989 | Japan . |
| A-01-290-662 | 11/1989 | Japan . |
| A-1-283274 | 11/1989 | Japan . |
| A-02-053776 | 2/1990 | Japan . |
| A-02-056-467 | 2/1990 | Japan . |
| A-2-292263 | 12/1990 | Japan . |
| A-2-300173 | 12/1990 | Japan . |
| A-2-305073 | 12/1990 | Japan . |
| A-3-93774 | 4/1991 | Japan . |
| A-3-120255 | 5/1991 | Japan . |
| A-4-112873 | 4/1992 | Japan . |
| A-4-224565 | 8/1992 | Japan . |
| 2020662 | 11/1979 | United Kingdom . |
| WO-95 29162 | 11/1995 | WIPO . |

OTHER PUBLICATIONS

M.F.A. Abdel–Lateef et al., Chemical Abstracts, vol. 81, p.142, 1974.
I. Okada et al., Chemical Abstracts, vol. 122, No. 7, 1995.
Bull. Soc. Chim. Fr., p. 293 (1966).
Chem. Ber. vol. 59, p. 1282 (1926).
Chem. Ber. vol. 59, p. 601 (1926).
J. Prak. Chem., vol. 143, p. 259 (1935).
Chemical Abstracts, vol. 40, p. 4056 (1946).
J. Chem. Soc., p. 87 (1946).
J. Heterocyclic Chem., vol. 22, p. 1621 (1985).
Chemical Abstracts, vol. 58, p. 3408 (1963).
Chemical Abstracts, vol. 61, p. 8298 (1964).

*Primary Examiner*—Robert W. Ramsuer
*Attorney, Agent, or Firm*—Oliff & Berridge, PLC

[57] ABSTRACT

The present invention provides a plant disease control agent containing as active ingredient one or more compounds of the formula [1]

$$A\text{—}COOR^1 \qquad [1]$$

wherein $R^1$ represents a hydrogen atom or a $C_1$–$C_4$ alkyl group, and

A represents a group of the formula (A-1) or (A-2)

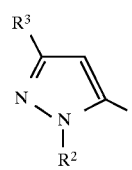

A-1 or

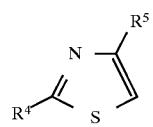

A-2

$R^2$ represents a $C_1$–$C_4$ alkyl group,
$R^3$ represents a $C_1$–$C_4$ alkyl group,
$R^4$ represents a halogen atom or a $C_1$–$C_4$ alkyl group, and
$R^5$ represents a $C_1$–$C_4$ alkyl group.
Further, the compound of A-1 in the formula [1] in which $R^3$ is a halogen atom is also included in the present invention.

7 Claims, No Drawings

PYRAZOLECARBOXYLIC ACID DERIVATIVES AND PLANT DISEASE CONTROL AGENT

FIELD OF THE INVENTION

The present invention relates to novel pyrazolecarboxylic acid derivatives, a plant disease control agent, especially, a paddy rice blast control agent, containing pyrazolecarboxylic acid derivatives or thiazolecarboxylic acid derivatives as an active ingredient.

TECHNICAL BACKGROUND

Some of 5-pyrazolecarboxylic acid derivatives have been already known as intermediates of medications and agricultural chemicals as described in, for example, Japanese Patent Application Laid-open No. Hei 2-292263, Japanese Patent Application Laid-open No. Hei 4-112873 and Japanese Patent Application Laid-open No. Hei 4-224565 and the literature references indicated therein.

Some of 5-thiazolecarboxylic acid derivatives have been already known as intermediates of medications and agricultural chemicals as described in, for example, Japanese Patent Application Laid-open No. Hei 2-305073 and the literature references indicated therein.

However, the above-mentioned laid-open publications and the literature references do not at all describe a plant disease controlling activity of these compounds. Further, 5-pyrazolecarboxylic acid derivatives containing a halogen atom in the 3-position are novel compounds undescribed in the documents.

None of the existing agricultural and horticultural microbicides are satisfactory with respect to the problems such as an increase in fungicide resistance and an environmental safety as well as an activity and a residual effect thereof. The development of less costly, useful plant disease control agents have been desired.

DISCLOSURE OF THE INVENTION

Under these circumstances, the present inventors have conducted investigations to develop compounds having an excellent microbicidal activity, and have consequently found that the compounds of the following formulas [1] and [2] exhibit an excellent microbicidal activity. This finding has led to the completion of the present invention.

That is, the present invention relates to a plant disease control agent containing as an active ingredient a compound of the formula [1]:

$$A-COOR^1 \quad [1]$$

wherein $R^1$ represents a hydrogen atom or a $C_1-C_4$ alkyl group,

A represents a group of the formula (A-1) or (A-2)

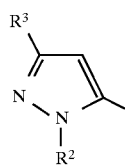

A-1 or

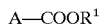

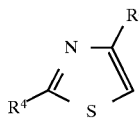

A-2

$R^2$ represents a $C_1-C_4$ alkyl group, $R^3$ represents a $C_1-C_4$ alkyl group, $R^4$ represents a halogen atom or a $C_1-C_4$ alkyl group, and $R^5$ represents a $C_1-C_4$ alkyl group.

Some of the compounds of the formula [1] are known compounds.

Further, the present invention relates to a novel pyrazolecarboxylic acid derivative of the formula [2]:

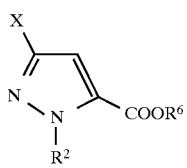

[2]

wherein

X represents a halogen atom, $R^2$ represents a $C^1-C_4$ alkyl group, $R^6$ represents a hydrogen atom, an alkali metal atom, an alkaline-earth metal atom, ammonium, sulfonium, phosphonium, an optionally substituted aryl group, an optionally substituted heteroaryl group, an optionally substituted heterocyclyl group, an optionally substituted aryl $C_2-C_4$ alkenyl group, $-[C(R^7)(R^8)]_m-R^9$, $-N(R^{10})(R^{11})$ or $-N=C(R^{12})(R^{13})$, $R^7$ and $R^8$, independently from each other, represent a hydrogen atom, a halogen atom, a $C_1-C_6$ alkyl group ($R^7$ and $R^8$ may together form a cyclic alkyl group), a $C_2-C_6$ alkenyl group, a $C_2-C_6$ alkynyl group, a $C_1-C_6$ haloalkyl group, an optionally substituted aryl group, an optionally substituted heteroaryl group, a $C_1-C_4$ alkylcarbonyl group, a $C_1-C_6$ alkoxycarbonyl group or a cyano group, m is 0 or 1 to 5, $R^9$ represents a hydrogen atom, a halogen atom, a $C_1-C_{10}$ alkyl group, a $C_2-C_{10}$ alkenyl group, a $C_2-C_{10}$ alkynyl group, a $C_1-C_{10}$ haloalkyl group, a $C_2-C_{10}$ haloalkenyl group, a $C_3-C_{10}$ cycloalkyl group, an optionally substituted aryl group, an optionally substituted heteroaryl group, an optionally substituted heterocyclyl group, a $C_1-C_6$ alkoxy group, a $C_1-C_6$ haloalkoxy group, a $C_2-C_6$ alkenyloxy group, a $C_2-C_6$ haloalkenyloxy group, a $C_2-C_6$ alkynyloxy group, a $C_3-C_8$ cycloalkyloxy group, a $C_1-C_6$ alkoxy $C_1-C_6$ alkyl group, an optionally substituted arylalkyloxy group, an optionally substituted aryloxy group, an optionally substituted heteroaryloxy group, a cyano group, $-C(O)-R^{14}$, $-S(O)_nR^{15}$, $-N(R^{16})(R^{17})$, $-ON=C(R^{18})(R^{19})$ or OH, $R^{10}$ and $R^{11}$, independently from each other, represent a hydrogen atom, a $C_1-C_6$ alkyl group, a $C_1-C_6$ haloalkyl group, a $C_2-C_6$ alkenyl group, a $C_2-C_6$ haloalkenyl group, a $C_2-C_6$ alkynyl group, a $C_1-C_4$ alkoxy $C_1-C_4$ alkyl group, a $C_1-C_4$ alkylthio $C_1-C_4$ alkyl group, a $C_1-C_6$ alkylcarbonyl group, a $C_1-C_6$ alkoxycarbonyl group, a $C_1-C_6$ alkylsulfonyl group, an optionally substituted aryl group, an optionally substituted arylcarbonyl group or an optionally substituted arylsulfonyl group, $R^{12}$ represents a $C_1$–$C_6$ alkyl group, a $C_1$–$C_6$ haloalkyl group or an optionally substituted aryl group, $R^{13}$ represents an amino group, a $C_1$–$C_6$ monoalkylamino group or a $C_1$–$C_5$ dialkylamino group, $R^{14}$ represents a hydrogen atom, OH, a $C_1$–$C_6$ alkyl group, a $C_1$–$C_6$ haloalkyl group, an optionally substituted aryl group, a $C_1$–$C_6$ alkoxy group, a $C_1$–$C_6$ haloalkoxy group, a $C_2$–$C_6$ alkenyloxy group, a $C_2$–$C_6$ haloalkenyloxy group, a $C_2$–$C_6$ alkynyloxy group or an optionally substituted heterocyclyloxy group, n is 0, 1 or 2, $R^{15}$ represents a hydrogen atom, a $C_1$–$C_6$ alkyl group, a $C_1$–$C_6$ haloalkyl group or a $C_2$–$C_6$ alkenyl group, $R^{16}$ and $R^{17}$, independently from each other, represent a hydrogen atom, a $C_1$–$C_6$ alkyl group ($R^{16}$ and $R^{17}$ may together form a cyclic alkyl group), a $C_3$–$C_6$ cycloalkyl group, an optionally substituted aryl group, an optionally substituted aryl $C_2$–$C_4$ alkyl group, a $C_1$–$C_6$ alkylcarbonyl group, an optionally substituted arylcarbonyl group or a $C_1$–$C_6$ alkoxycarbonyl group, $R^{18}$ and $R^{19}$, independently from each other, represent a hydrogen atom, a $C_1$–$C_6$ alkyl group or an optionally substituted aryl group, the expression "optionally substituted" means unsubstituted or substituted with 1 to 9 groups selected from a halogen atom, a cyano group, a nitro group, a $C_1$–$C_4$ alkyl group, a $C_1$–$C_4$ alkoxy group, a $C_1$–$C_4$ haloalkyl group, a $C_1$–$C_4$ haloalkoxy group, an aryl group, an aryloxy group, a benzyl group, a benzyloxy group, a $C_3$–$C_6$ cycloalkyl group, a $C_1$–$C_4$ alkoxycarbonyl group, a $C_1$–$C_4$ alkylthio group, a $C_1$–$C_4$ alkylsulfinyl, a $C_1$–$C_4$ alkylsulfonyl group, a styryl group, an amino group, a $C_1$–$C_4$ alkoxycarbonylamino group, a $C_1$–$C_4$ alkoxycarbonyloxy group and/or an aminocarbonyl group, the "aryl" group means a residue obtained by removing one hydrogen atom bound to a carbon atom of an aromatic ring from an aromatic hydrocarbon compound, the "heteroaryl" group means a residue obtained by removing one hydrogen atom bound to a carbon atom of a heterocyclic ring from a 5-membered or 6-membered aromatic heterocyclic compound, and the "heterocyclyl group" means a residue obtained by removing a hydrogen atom bound to a carbon atom of a heterocyclic ring from a 3- to 6-membered non-aromatic heterocyclic compound; and to a plant disease control agent containing the above-mentioned derivative as an active ingredient.

In the compound of the formula [1], A is a group of the formula [A-1] or [A-2]. Examples of the $C_1$–$C_4$ alkyl group of $R^1$ to $R^5$ include a methyl group, an ethyl group, an n- or i-propyl group, and an n-, s-, i- or tert-butyl group. Examples of the halogen atom of $R^4$ include a chlorine atom, a bromine atom, a fluorine atom and an iodine atom.

Preferably, $R^2$ and $R^3$ are methyl groups, $R^4$ is a chlorine atom or a methyl group, and $R^5$ is a methyl group or an ethyl group.

In the compound of the formula [2], it is a structural characteristic feature of the compounds of the present invention that X is a halogen atom and $R^2$ is a $C_1$–$C_4$ alkyl group. Examples of the halogen atom include a chlorine atom, a bromine atom, a fluorine atom and an iodine atom. The chlorine atom or the bromine atom is especially preferable. Examples of the $C_1$–$C_4$ alkyl group include a methyl group, an ethyl group, an n- or i-propyl group and an n-, s-, i- or tert-butyl group. The methyl group is especially preferable.

$R^6$ is not particularly limited. Especially, $R^6$ represents —[C($R^7$)($R^8$)]$_m$—$R^9$ in which $R^7$ and $R^8$ each represent a hydrogen atom, a methyl group or an ethyl group, $R^9$ represents a hydrogen atom, a $C_1$–$C_{10}$ alkyl group or an optionally substituted aryl group, and m is 0 to 2. Preferable examples thereof include a methyl group, an ethyl group, a propyl group, a butyl group, a phenyl group, a benzyl group, a 2-phenylethyl group or a 2-phenylpropyl group.

The definitions for the substituents of $R^6$ are as follows.

The halogen atom means a fluorine, chlorine, bromine or iodine atom.

Examples of the $C_1$–$C_4$ alkyl group, the $C_1$–$C_6$ alkyl group and the $C_1$–$C_{10}$ alkyl group include a methyl group, an ethyl group, an n- or i-propyl group, an n-, s-, i- or tert-butyl group, a pentyl group, a hexyl group, an octyl group, a nonyl group and an octyl group.

Examples of the aryl group include a phenyl group, a naphthyl group and an anthranyl group.

Examples of the heteroaryl group include a furyl group, a thienyl group, a pyrrolyl group, a pyrazolyl group, an imidazolyl group, a pyridyl group, a pyrimidinyl group, a pyridazinyl group and a pyrazinyl group.

Examples of the heterocyclyl group include an oxiranyl group, an oxetanyl group, a tetrahydrofuryl group, a dioxolanyl group, a tetrahydropyranyl group, a dioxanyl group, a thiiranyl group, a tetrahydrothienyl group, a pyrrolidinyl group, a piperidyl group, a piperazinyl group, a morpholinylgroup and a thiomorpholinyl group.

The compounds of the present invention exhibits almost no or very weak antimicrobial activity against paddy rice blast microbes in experiments using laboratory dish. However, when the compounds are applied to a paddy either directly or on water surface, they exhibit an excellent activity of controlling the paddy rice blast disease. That is, it is considered that the compounds of the present invention expedite production of antimicrobial products within the paddy rice and imparts resistance to the disease, thereby controlling infection of the paddy rice blast microbes and preventing the attack of the disease.

Among the above-mentioned plant disease control agents, especially paddy rice blast control agents in the present invention, preferable groups are mentioned below.

(1) a plant disease control agent in which A is a group of the formula (A-1);

(2) a plant disease control agent in which A represents a group of the formula (A-1), $R^2$ represents a methyl group, and $R^3$ represents a methyl group;

(3) a plant disease control agent in which A represents a group of the formula (A-2); and (4) a plant disease control agent in which A represents a group of the formula (A-2), $R^4$ represents a chlorine atom or a methyl group, and $R^5$ represents a methyl group or an ethyl group.

Among the pyrazolecarboxylic acid derivatives of the formula [2] in the present invention, preferable groups are mentioned below.

(5) pyrazolecarboxylic acid derivatives of the formula in which X represents a chlorine atom or a bromine atom, and $R^2$ represents a methyl group;

(6) pyrazolecarboxylic acid derivatives of the formula in which X represents a chlorine atom or a bromine atom, $R^2$ represents a methyl group, and $R^6$ represents —[C($R^7$)($R^8$)]$_m$—$R^9$ group (wherein $R^7$, $R^8$, $R^9$ and m have the same meanings as defined above);

(7) pyrazolecarboxylic acid derivatives of the formula in which X represents a chlorine atom, $R^2$ represents a methyl group, $R^6$ represents $—[C(R^7)(R^8)]_m—R^9$ group (wherein $R^7$ and $R^8$, independently from each other, represent a hydrogen atom, a methyl group or an ethyl group, $R^9$ represents a hydrogen atom, a $C_1$–$C_{10}$ alkyl group or an optionally substituted aryl group, and m is 0, 1 or 2); and (8) pyrazolecarboxylic acid derivatives of the formula in which X represents a chlorine atom, $R^2$ represents a methyl group, and $R^6$ represents a methyl group, an ethyl group, a propyl group, a butyl group, a phenyl group, a benzyl group, a 2-phenylethyl group or a 2-phenylpropyl group.

A plant disease control agent, especially, a paddy rice blast control agent containing as an active ingredient at least one of the above-mentioned pyrazolecarboxylic acid derivatives of the formula [2] and the groups (5) to (8) thereof is also included in the present invention.

Examples of the active ingredient of the formula [1] in the plant disease control agent of the present invention are shown in Tables 1 and 2.

However, the compounds of the present invention are not limited thereto.

In these tables, Me indicates a methyl group, Et indicates an ethyl group, Pr indicates a propyl group, Bu indicates a butyl group, i indicates iso, s indicates secondary, and t indicates tertiary.

TABLE 1

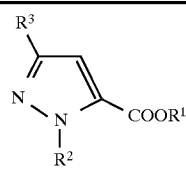

| Compound No. | $R^3$ | $R^2$ | $R^1$ |
|---|---|---|---|
| 1.1 | Me | Me | H |
| 1.2 | Me | Me | Me |
| 1.3 | Me | Me | Et |
| 1.4 | Me | Me | Pr |
| 1.5 | Me | Me | i-Pr |
| 1.6 | Me | Me | Bu |
| 1.7 | Me | Me | s-Bu |
| 1.8 | Me | Me | t-Bu |
| 1.9 | Et | Me | H |
| 1.10 | Et | Me | Me |
| 1.11 | Et | Me | Et |
| 1.12 | Pr | Me | H |
| 1.13 | Pr | Me | Me |
| 1.14 | Pr | Me | Et |
| 1.15 | Bu | Me | H |
| 1.16 | Bu | Me | Me |
| 1.17 | Bu | Me | Et |
| 1.18 | Me | Et | H |
| 1.19 | Me | Et | Me |
| 1.20 | Me | Et | Et |
| 1.21 | Me | Pr | H |
| 1.22 | Me | Pr | Me |
| 1.23 | Me | Pr | Et |
| 1.24 | Me | Bu | H |
| 1.25 | Me | Bu | Me |
| 1.26 | Me | Bu | Et |

TABLE 2

| Compound No. | $R^4$ | $R^5$ | $R^1$ |
|---|---|---|---|
| 2.1 | Me | Me | H |
| 2.2 | Me | Me | Me |
| 2.3 | Me | Me | Et |
| 2.4 | Me | Me | Pr |
| 2.5 | Me | Me | i-Pr |
| 2.6 | Me | Me | Bu |
| 2.7 | Me | Me | s-Bu |
| 2.8 | Me | Me | t-Bu |
| 2.9 | Et | Me | H |
| 2.10 | Et | Me | Me |
| 2.11 | Et | Me | Et |
| 2.12 | Pr | Me | H |
| 2.13 | Pr | Me | Me |
| 2.14 | Pr | Me | Et |
| 2.15 | Bu | Me | H |
| 2.16 | Bu | Me | Me |
| 2.17 | Bu | Me | Et |
| 2.18 | Me | Et | H |
| 2.19 | Me | Et | Me |
| 2.20 | Me | Et | Et |
| 2.21 | Me | Et | Pr |
| 2.22 | Me | Et | i-Pr |
| 2.23 | Me | Et | Bu |
| 2.24 | Me | Et | s-Bu |
| 2.25 | Me | Et | t-Bu |
| 2.26 | Me | Pr | H |
| 2.27 | Me | Pr | Me |
| 2.28 | Me | Pr | Et |
| 2.29 | Me | Bu | H |
| 2.30 | Me | Bu | Me |
| 2.31 | Me | Bu | Et |
| 2.32 | Cl | Me | H |
| 2.33 | Cl | Me | Me |
| 2.34 | Cl | Me | Et |
| 2.35 | Cl | Me | Pr |
| 2.36 | Cl | Me | i-Pr |
| 2.37 | Cl | Me | Bu |
| 2.38 | Cl | Me | s-Bu |
| 2.39 | Cl | Me | t-Bu |
| 2.40 | Cl | Et | H |
| 2.41 | Cl | Et | Me |
| 2.42 | Cl | Et | Et |
| 2.43 | Cl | Pr | H |
| 2.44 | Cl | Bu | H |
| 2.45 | Br | Me | H |
| 2.46 | Br | Me | Me |
| 2.47 | Br | Me | Et |
| 2.48 | F | Me | H |

Next, the compounds of the present invention of the formula [2] are shown in Tables 3 to 6.

However, the compounds of the present invention are not to be limited thereto.

In the tables, Me indicates a methyl group, Et does an ethyl group, Pr does a propyl group, Bu does a butyl group, Pen does a pentyl group, Hex does a hexyl group, Ph does a phenyl group, i does iso, s- does secondary, t- does tertiary, and cyc- does cyclo.

TABLE 3

In the compounds of (a) 5-Cl, 1-Me pyrazole-3-carboxylate-O-D-phenyl-B (b) 5-Cl, 1-Et pyrazole-3-carboxylate-O-D-phenyl-B (c) 5-Cl, 1-Pr pyrazole-3-carboxylate-O-D-phenyl-B (d) 5-Cl, 1-iPr pyrazole-3-carboxylate-O-D-phenyl-B (e) 5-Cl, 1-Bu pyrazole-3-carboxylate-O-D-phenyl-B (f) 5-Cl, 1-tBu pyrazole-3-carboxylate-O-D-phenyl-B or (g) 5-Br, 1-Me pyrazole-3-carboxylate-O-D-phenyl-B

| Compound No. | B | D |
|---|---|---|
| 3.1 | H | — |
| 3.2 | 2-Me | — |
| 3.3 | 3-Me | — |
| 3.4 | 4-Me | — |
| 3.5 | 2-Et | — |
| 3.6 | 3-Et | — |
| 3.7 | 4-Et | — |
| 3.8 | 2-Pr | — |
| 3.9 | 3-Pr | — |
| 3.10 | 4-Pr | — |
| 3.11 | 2-i-Pr | — |
| 3.12 | 3-i-Pr | — |
| 3.13 | 4-i-Pr | — |
| 3.14 | 2-t-Bu | — |
| 3.15 | 3-t-Bu | — |
| 3.16 | 4-t-Bu | — |
| 3.17 | 2,4-Me$_2$ | — |
| 3.18 | 2,5-Me$_2$ | — |
| 3.19 | 2,6-Me$_2$ | — |
| 3.20 | 3,4-Me$_2$ | — |
| 3.21 | 2,4,6-Me$_3$ | — |
| 3.22 | 4-t-Bu-2,6-Me$_2$ | — |
| 3.23 | 3,5-(t-Bu)$_2$-4-OH | — |
| 3.24 | 2-CF$_3$ | — |
| 3.25 | 3-CF$_3$ | — |
| 3.26 | 4-CF$_3$ | — |
| 3.27 | 2-Cl | — |
| 3.28 | 3-Cl | — |
| 3.29 | 4-Cl | — |
| 3.30 | 2,4-Cl$_2$ | — |
| 3.31 | 2,5-Cl$_2$ | — |
| 3.32 | 2,6-Cl$_2$ | — |
| 3.33 | 3,4-Cl$_2$ | — |
| 3.34 | 2,4,6-Cl$_3$ | — |
| 3.35 | 2-F | — |
| 3.36 | 3-F | — |
| 3.37 | 4-F | — |
| 3.38 | 2,4-F$_2$ | — |
| 3.39 | 3,4-F$_2$ | — |
| 3.40 | 2,6-F$_2$ | — |
| 3.41 | 2-Cl-6-F | — |
| 3.42 | 2-Br | — |
| 3.43 | 3-Br | — |
| 3.44 | 4-Br | — |
| 3.45 | 2,4-Br$_2$ | — |
| 3.46 | 2,6-Br$_2$ | — |
| 3.47 | 3,4-Br$_2$ | — |
| 3.48 | 4-I | — |
| 3.49 | 4-Cl-2-Me | — |
| 3.50 | 2-NO$_2$ | — |
| 3.51 | 3-NO$_2$ | — |
| 3.52 | 4-NO$_2$ | — |
| 3.53 | 2-Cl-4-NO$_2$ | — |
| 3.54 | 3-Cl-4-NO$_2$ | — |
| 3.55 | 4-Cl-3-NO$_2$ | — |
| 3.56 | 4-OH | — |
| 3.57 | 2-OMe | — |
| 3.58 | 3-OMe | — |
| 3.59 | 4-OMe | — |
| 3.60 | 4-OBu | — |
| 3.61 | 3,4-(OMe)$_2$ | — |
| 3.62 | 4-SMe | — |
| 3.63 | 4-SOMe | — |
| 3.64 | 4-SO$_2$Me | — |
| 3.65 | 4-OCHF$_2$ | — |
| 3.66 | 4-OCF$_3$ | — |
| 3.67 | 2-Ph | — |
| 3.68 | 3-Ph | — |
| 3.69 | 4-Ph | — |
| 3.70 | 2-OPh | — |
| 3.71 | 3-OPh | — |
| 3.72 | 4-OPh | — |
| 3.73 | 2-OCH$_2$Ph | — |
| 3.74 | 3-OCH$_2$Ph | — |
| 3.75 | 4-OCH$_2$Ph | — |
| 3.76 | 4-CH=CH—Ph | — |
| 3.77 | 4-NH$_2$ | — |
| 3.78 | 4-NMe$_2$ | — |
| 3.79 | 4-OCO$_2$Me | — |
| 3.80 | 4-OCO$_2$Et | — |
| 3.81 | 4-OCO$_2$t-Bu | — |
| 3.82 | 3-Cl-4-OCO$_2$t-Bu | — |
| 3.83 | 4-NHCO$_2$Me | — |
| 3.84 | 4-NHCO$_2$Et | — |
| 3.85 | 4-NHCO$_2$t-Bu | — |
| 3.86 | 4-CO$_2$Me | — |
| 3.87 | 4-CO$_2$Et | — |
| 3.88 | 4-CONHMe | — |
| 3.89 | 4-CONHEt | — |
| 3.90 | 4-CONMe$_2$ | — |
| 3.91 | 4-CONEt$_2$ | — |
| 3.92 | 4-CN | — |
| 3.93 | H | CH$_2$ |

TABLE 3-continued

| | | |
|---|---|---|
| 3.94 | 2-Me | $CH_2$ |
| 3.95 | 3-Me | $CH_2$ |
| 3.96 | 4-Me | $CH_2$ |
| 3.97 | 2-Et | $CH_2$ |
| 3.98 | 3-Et | $CH_2$ |
| 3.99 | 4-Et | $CH_2$ |
| 3.100 | 2-Pr | $CH_2$ |
| 3.101 | 3-Pr | $CH_2$ |
| 3.102 | 4-Pr | $CH_2$ |
| 3.103 | 2-i-Pr | $CH_2$ |
| 3.104 | 3-i-Pr | $CH_2$ |
| 3.105 | 4-i-Pr | $CH_2$ |
| 3.106 | 2-t-Bu | $CH_2$ |
| 3.107 | 3-t-Bu | $CH_2$ |
| 3.108 | 4-t-Bu | $CH_2$ |
| 3.109 | 2,4-$Me_2$ | $CH_2$ |
| 3.110 | 2,5-$Me_2$ | $CH_2$ |
| 3.111 | 2,6-$Me_2$ | $CH_2$ |
| 3.112 | 3,4-$Me_2$ | $CH_2$ |
| 3.113 | 2,4,6-$Me_3$ | $CH_2$ |
| 3.114 | 4-t-Bu-2,6-$Me_2$ | $CH_2$ |
| 3.115 | 3,5-$(t-Bu)_2$-4-OH | $CH_2$ |
| 3.116 | 2-$CF_3$ | $CH_2$ |
| 3.117 | 3-$CF_3$ | $CH_2$ |
| 3.118 | 4-$CF_3$ | $CH_2$ |
| 3.119 | 2-Cl | $CH_2$ |
| 3.120 | 3-Cl | $CH_2$ |
| 3.121 | 4-Cl | $CH_2$ |
| 3.122 | 2,4-$Cl_2$ | $CH_2$ |
| 3.123 | 2,5-$Cl_2$ | $CH_2$ |
| 3.124 | 2,6-$Cl_2$ | $CH_2$ |
| 3.125 | 3,4-$Cl_2$ | $CH_2$ |
| 3.126 | 2,4,6-$Cl_3$ | $CH_2$ |
| 3.127 | 2-F | $CH_2$ |
| 3.128 | 3-F | $CH_2$ |
| 3.129 | 4-F | $CH_2$ |
| 3.130 | 2,4-$F_2$ | $CH_2$ |
| 3.131 | 3,4-$F_2$ | $CH_2$ |
| 3.132 | 2,6-$F_2$ | $CH_2$ |
| 3.133 | 2-Cl-6-F | $CH_2$ |
| 3.134 | 2-Br | $CH_2$ |
| 3.135 | 3-Br | $CH_2$ |
| 3.136 | 4-Br | $CH_2$ |
| 3.137 | 2,4-$Br_2$ | $CH_2$ |
| 3.138 | 2,6-$Br_2$ | $CH_2$ |
| 3.139 | 3,4-$Br_2$ | $CH_2$ |
| 3.140 | 4-I | $CH_2$ |
| 3.141 | 4-Cl-2-Me | $CH_2$ |
| 3.142 | 2-$NO_2$ | $CH_2$ |
| 3.143 | 3-$NO_2$ | $CH_2$ |
| 3.144 | 4-$NO_2$ | $CH_2$ |
| 3.145 | 2-Cl-4-$NO_2$ | $CH_2$ |
| 3.146 | 3-Cl-4-$NO_2$ | $CH_2$ |
| 3.147 | 4-Cl-3-$NO_2$ | $CH_2$ |
| 3.148 | 4-OH | $CH_2$ |
| 3.149 | 2-OMe | $CH_2$ |
| 3.150 | 3-OMe | $CH_2$ |
| 3.151 | 4-OMe | $CH_2$ |
| 3.152 | 4-OBu | $CH_2$ |
| 3.153 | 3,4-$(OMe)_2$ | $CH_2$ |
| 3.154 | 4-SMe | $CH_2$ |
| 3.155 | 4-SOMe | $CH_2$ |
| 3.156 | 4-$SO_2Me$ | $CH_2$ |
| 3.157 | 4-$OCHF_2$ | $CH_2$ |
| 3.158 | 4-$OCF_3$ | $CH_2$ |
| 3.159 | 2-Ph | $CH_2$ |
| 3.160 | 3-Ph | $CH_2$ |
| 3.161 | 4-Ph | $CH_2$ |
| 3.162 | 2-OPh | $CH_2$ |
| 3.163 | 3-OPh | $CH_2$ |
| 3.164 | 4-OPh | $CH_2$ |
| 3.165 | 2-$OCH_2Ph$ | $CH_2$ |
| 3.166 | 3-$OCH_2Ph$ | $CH_2$ |
| 3.167 | 4-$OCH_2Ph$ | $CH_2$ |
| 3.168 | 4-CH=CH—Ph | $CH_2$ |
| 3.169 | 4-$NH_2$ | $CH_2$ |
| 3.170 | 4-$NMe_2$ | $CH_2$ |
| 3.171 | 4-$OCO_2Me$ | $CH_2$ |
| 3.172 | 4-$OCO_2Et$ | $CH_2$ |
| 3.173 | 4-$OCO_2t$-Bu | $CH_2$ |
| 3.174 | 3-Cl-4-$OCO_2t$-Bu | $CH_2$ |
| 3.175 | 4-$NHCO_2Me$ | $CH_2$ |
| 3.176 | 4-$NHCO_2Et$ | $CH_2$ |
| 3.177 | 4-$NHCO_2t$-Bu | $CH_2$ |
| 3.178 | 4-$CO_2Me$ | $CH_2$ |
| 3.179 | 4-$CO_2Et$ | $CH_2$ |
| 3.180 | 4-CONHMe | $CH_2$ |
| 3.181 | 4-CONHEt | $CH_2$ |
| 3.182 | 4-$CONMe_2$ | $CH_2$ |
| 3.183 | 4-$CONEt_2$ | $CH_2$ |
| 3.184 | 4-CN | $CH_2$ |
| 3.185 | H | $(CH_2)_2$ |
| 3.186 | 2-Me | $(CH_2)_2$ |
| 3.187 | 3-Me | $(CH_2)_2$ |
| 3.188 | 4-Me | $(CH_2)_2$ |
| 3.189 | 4-Et | $(CH_2)_2$ |
| 3.190 | 4-i-Pr | $(CH_2)_2$ |
| 3.191 | 4-t-Bu | $(CH_2)_2$ |
| 3.192 | 2,4-$Me_2$ | $(CH_2)_2$ |
| 3.193 | 2,6-$Me_2$ | $(CH_2)_2$ |
| 3.194 | 3,4-$Me_2$ | $(CH_2)_2$ |
| 3.195 | 4-$CF_3$ | $(CH_2)_2$ |
| 3.196 | 2-Cl | $(CH_2)_2$ |
| 3.197 | 3-Cl | $(CH_2)_2$ |
| 3.198 | 4-Cl | $(CH_2)_2$ |
| 3.199 | 2,4-$Cl_2$ | $(CH_2)_2$ |
| 3.200 | 2,6-$Cl_2$ | $(CH_2)_2$ |
| 3.201 | 2-F | $(CH_2)_2$ |
| 3.202 | 3-F | $(CH_2)_2$ |
| 3.203 | 4-F | $(CH_2)_2$ |
| 3.204 | 2,4-$F_2$ | $(CH_2)_2$ |
| 3.205 | 2,6-$F_2$ | $(CH_2)_2$ |
| 3.206 | 4-Br | $(CH_2)_2$ |
| 3.207 | 2,4-$Br_2$ | $(CH_2)_2$ |
| 3.208 | 4-I | $(CH_2)_2$ |
| 3.209 | 4-$NO_2$ | $(CH_2)_2$ |
| 3.210 | 4-OMe | $(CH_2)_2$ |
| 3.211 | 3,4-$(OMe)_2$ | $(CH_2)_2$ |
| 3.212 | 4-SMe | $(CH_2)_2$ |
| 3.213 | 4-$SO_2Me$ | $(CH_2)_2$ |
| 3.214 | 4-$OCHF_2$ | $(CH_2)_2$ |
| 3.215 | 4-$OCF_3$ | $(CH_2)_2$ |
| 3.216 | 4-Ph | $(CH_2)_2$ |
| 3.217 | 2-OPh | $(CH_2)_2$ |
| 3.218 | 3-OPh | $(CH_2)_2$ |
| 3.219 | 4-OPh | $(CH_2)_2$ |
| 3.220 | 2-$OCH_2Ph$ | $(CH_2)_2$ |
| 3.221 | 3-$OCH_2Ph$ | $(CH_2)_2$ |
| 3.222 | 4-$OCH_2Ph$ | $(CH_2)_2$ |
| 3.223 | 4-CH=CH—Ph | $(CH_2)_2$ |
| 3.224 | 4-$NH_2$ | $(CH_2)_2$ |
| 3.225 | 4-$OCO_2Et$ | $(CH_2)_2$ |
| 3.226 | 4-$NHCO_2Et$ | $(CH_2)_2$ |
| 3.227 | 4-$CO_2Et$ | $(CH_2)_2$ |
| 3.228 | 4-$CONMe_2$ | $(CH_2)_2$ |
| 3.229 | H | CHMe |
| 3.230 | 2-Me | CHMe |
| 3.231 | 3-Me | CHMe |
| 3.232 | 4-Me | CHMe |
| 3.233 | 4-Et | CHMe |
| 3.234 | 4-i-Pr | CHMe |
| 3.235 | 4-t-Bu | CHMe |
| 3.236 | 2,4-$Me_2$ | CHMe |
| 3.237 | 2,6-$Me_2$ | CHMe |
| 3.238 | 3,4-$Me_2$ | CHMe |
| 3.239 | 4-$CF_3$ | CHMe |
| 3.240 | 2-Cl | CHMe |
| 3.241 | 3-Cl | CHMe |
| 3.242 | 4-Cl | CHMe |
| 3.243 | 2,4-$Cl_2$ | CHMe |
| 3.244 | 2,6-$Cl_2$ | CHMe |
| 3.245 | 2-F | CHMe |
| 3.246 | 3-F | CHMe |
| 3.247 | 4-F | CHMe |
| 3.248 | 2,4-$F_2$ | CHMe |
| 3.249 | 2,6-$F_2$ | CHMe |
| 3.250 | 4-Br | CHMe |
| 3.251 | 2,4-$Br_2$ | CHMe |

TABLE 3-continued

| | | |
|---|---|---|
| 3.252 | 4-I | CHMe |
| 3.253 | 4-NO$_2$ | CHMe |
| 3.254 | 4-OMe | CHMe |
| 3.255 | 3,4-(OMe)$_2$ | CHMe |
| 3.256 | 4-SMe | CHMe |
| 3.257 | 4-SO$_2$Me | CHMe |
| 3.258 | 4-OCHF$_2$ | CHMe |
| 3.259 | 4-OCF$_3$ | CHMe |
| 3.260 | 4-Ph | CHMe |
| 3.261 | 2-OPh | CHMe |
| 3.262 | 3-OPh | CHMe |
| 3.263 | 4-OPh | CHMe |
| 3.264 | 2-OCH$_2$Ph | CHMe |
| 3.265 | 3-OCH$_2$Ph | CHMe |
| 3.266 | 4-OCH$_2$Ph | CHMe |
| 3.267 | 4-CH=CH—Ph | CHMe |
| 3.268 | 4-NH$_2$ | CHMe |
| 3.269 | 4-OCO$_2$Et | CHMe |
| 3.270 | 4-NHCO$_2$Et | CHMe |
| 3.271 | 4-CO$_2$Et | CHMe |
| 3.272 | 4-CONMe$_2$ | CHMe |
| 3.273 | H | (CH$_2$)$_3$ |
| 3.274 | 2-Me | (CH$_2$)$_3$ |
| 3.275 | 3-Me | (CH$_2$)$_3$ |
| 3.276 | 4-Me | (CH$_2$)$_3$ |
| 3.277 | 4-Et | (CH$_2$)$_3$ |
| 3.278 | 4-i-Pr | (CH$_2$)$_3$ |
| 3.279 | 4-t-Bu | (CH$_2$)$_3$ |
| 3.280 | 2,4-Me$_2$ | (CH$_2$)$_3$ |
| 3.281 | 2,6-Me$_2$ | (CH$_2$)$_3$ |
| 3.282 | 3,4-Me$_2$ | (CH$_2$)$_3$ |
| 3.283 | 4-CF$_3$ | (CH$_2$)$_3$ |
| 3.284 | 2-Cl | (CH$_2$)$_3$ |
| 3.285 | 3-Cl | (CH$_2$)$_3$ |
| 3.286 | 4-Cl | (CH$_2$)$_3$ |
| 3.287 | 2,4-Cl$_2$ | (CH$_2$)$_3$ |
| 3.288 | 2,6-Cl$_2$ | (CH$_2$)$_3$ |
| 3.289 | 2-F | (CH$_2$)$_3$ |
| 3.290 | 3-F | (CH$_2$)$_3$ |
| 3.291 | 4-F | (CH$_2$)$_3$ |
| 3.292 | 2,4-F$_2$ | (CH$_2$)$_3$ |
| 3.293 | 2,6-F$_2$ | (CH$_2$)$_3$ |
| 3.294 | 4-Br | (CH$_2$)$_3$ |
| 3.295 | 2,4-Br$_2$ | (CH$_2$)$_3$ |
| 3.296 | 4-I | (CH$_2$)$_3$ |
| 3.297 | 4-NO$_2$ | (CH$_2$)$_3$ |
| 3.298 | 4-OMe | (CH$_2$)$_3$ |
| 3.299 | 3,4-(OMe)$_2$ | (CH$_2$)$_3$ |
| 3.300 | 4-SMe | (CH$_2$)$_3$ |
| 3.301 | 4-SO$_2$Me | (CH$_2$)$_3$ |
| 3.302 | 4-OCHF$_2$ | (CH$_2$)$_3$ |
| 3.303 | 4-OCF$_2$ | (CH$_2$)$_3$ |
| 3.304 | 4-Ph | (CH$_2$)$_3$ |
| 3.305 | 2-OPh | (CH$_2$)$_3$ |
| 3.306 | 3-OPh | (CH$_2$)$_3$ |
| 3.307 | 4-OPh | (CH$_2$)$_3$ |
| 3.308 | 2-OCH$_2$Ph | (CH$_2$)$_3$ |
| 3.309 | 3-OCH$_2$Ph | (CH$_2$)$_3$ |
| 3.310 | 4-OCH$_2$Ph | (CH$_2$)$_3$ |
| 3.311 | 4-CH=CH—Ph | (CH$_2$)$_3$ |
| 3.312 | 4-NH$_2$ | (CH$_2$)$_3$ |
| 3.313 | 4-OCO$_2$Et | (CH$_2$)$_3$ |
| 3.314 | 4-NHCO$_2$Et | (CH$_2$)$_3$ |
| 3.315 | 4-CO$_2$Et | (CH$_2$)$_3$ |
| 3.316 | 4-CONMe$_2$ | (CH$_2$)$_3$ |
| 3.317 | H | CH$_2$CHMe |
| 3.318 | 2-Me | CH$_2$CHMe |
| 3.319 | 4-Me | CH$_2$CHMe |
| 3.320 | 4-Et | CH$_2$CHMe |
| 3.321 | 4-t-Bu | CH$_2$CHMe |
| 3.322 | 2,4-Me$_2$ | CH$_2$CHMe |
| 3.323 | 2,6-Me$_2$ | CH$_2$CHMe |
| 3.324 | 3,4-Me$_2$ | CH$_2$CHMe |
| 3.325 | 4-CF$_3$ | CH$_2$CHMe |
| 3.326 | 2-Cl | CH$_2$CHMe |
| 3.327 | 4-Cl | CH$_2$CHMe |
| 3.328 | 2,4-Cl$_2$ | CH$_2$CHMe |
| 3.329 | 2,6-Cl$_2$ | CH$_2$CHMe |
| 3.330 | 2-F | CH$_2$CHMe |
| 3.331 | 4-F | CH$_2$CHMe |
| 3.332 | 2,4-F$_2$ | CH$_2$CHMe |
| 3.333 | 2,6-F$_2$ | CH$_2$CHMe |
| 3.334 | 4-Br | CH$_2$CHMe |
| 3.335 | 4-NO$_2$ | CH$_2$CHMe |
| 3.336 | 4-OMe | CH$_2$CHMe |
| 3.337 | 4-SMe | CH$_2$CHMe |
| 3.338 | 4-SO$_2$Me | CH$_2$CHMe |
| 3.339 | 4-OCHF$_2$ | CH$_2$CHMe |
| 3.340 | 4-OCF$_3$ | CH$_2$CHMe |
| 3.341 | 4-Ph | CH$_2$CHMe |
| 3.342 | 4-OPh | CH$_2$CHMe |
| 3.343 | 4-OCH$_2$Ph | CH$_2$CHMe |
| 3.344 | 4-CH=CH—Ph | CH$_2$CHMe |
| 3.345 | 4-NH$_2$ | CH$_2$CHMe |
| 3.346 | 4-OCO$_2$Et | CH$_2$CHMe |
| 3.347 | 4-NHCO$_2$Et | CH$_2$CHMe |
| 3.348 | 4-CO$_2$Et | CH$_2$CHMe |
| 3.349 | 4-CONMe$_2$ | CH$_2$CHMe |
| 3.350 | H | CH(Me)CH$_2$ |
| 3.351 | 2-Me | CH(Me)CH$_2$ |
| 3.352 | 4-Me | CH(Me)CH$_2$ |
| 3.353 | 4-Et | CH(Me)CH$_2$ |
| 3.354 | 4-t-Bu | CH(Me)CH$_2$ |
| 3.355 | 2,4-Me$_2$ | CH(Me)CH$_2$ |
| 3.356 | 2,6-Me$_2$ | CH(Me)CH$_2$ |
| 3.357 | 3,4-Me$_2$ | CH(Me)CH$_2$ |
| 3.358 | 4-CF$_3$ | CH(Me)CH$_2$ |
| 3.359 | 2-Cl | CH(Me)CH$_2$ |
| 3.360 | 4-Cl | CH(Me)CH$_2$ |
| 3.361 | 2,4-Cl$_2$ | CH(Me)CH$_2$ |
| 3.362 | 2,6-Cl$_2$ | CH(Me)CH$_2$ |
| 3.363 | 2-F | CH(Me)CH$_2$ |
| 3.364 | 4-F | CH(Me)CH$_2$ |
| 3.365 | 2,4-F$_2$ | CH(Me)CH$_2$ |
| 3.366 | 2,6-F$_2$ | CH(Me)CH$_2$ |
| 3.367 | 4-Br | CH(Me)CH$_2$ |
| 3.368 | 4-NO$_2$ | CH(Me)CH$_2$ |
| 3.369 | 4-OMe | CH(Me)CH$_2$ |
| 3.370 | 4-SMe | CH(Me)CH$_2$ |
| 3.371 | 4-SO$_2$Me | CH(Me)CH$_2$ |
| 3.372 | 4-OCHF$_2$ | CH(Me)CH$_2$ |
| 3.373 | 4-OCF$_3$ | CH(Me)CH$_2$ |
| 3.374 | 4-Ph | CH(Me)CH$_2$ |
| 3.375 | 4-OPh | CH(Me)CH$_2$ |
| 3.376 | 4-OCh$_2$Ph | CH(Me)CH$_2$ |
| 3.377 | 4-CH=CH—Ph | CH(Me)CH$_2$ |
| 3.378 | 4-NH$_2$ | CH(Me)CH$_2$ |
| 3.379 | 4-OCO$_2$Et | CH(Me)CH$_2$ |
| 3.380 | 4-NHCO$_2$Et | CH(Me)CH$_2$ |
| 3.381 | 4-CO$_2$Et | CH(Me)CH$_2$ |
| 3.382 | 4-CONMe$_2$ | CH(Me)CH$_2$ |
| 3.383 | H | (CH$_2$)$_4$ |
| 3.384 | 2-Me | (CH$_2$)$_4$ |
| 3.385 | 4-Me | (CH$_2$)$_4$ |
| 3.386 | 4-Et | (CH$_2$)$_4$ |
| 3.387 | 4-t-Bu | (CH$_2$)$_4$ |
| 3.388 | 2,4-Me$_2$ | (CH$_2$)$_4$ |
| 3.389 | 2,6-Me$_2$ | (CH$_2$)$_4$ |
| 3.390 | 3,4-Me$_2$ | (CH$_2$)$_4$ |
| 3.391 | 4-CF$_3$ | (CH$_2$)$_4$ |
| 3.392 | 2-Cl | (CH$_2$)$_4$ |
| 3.393 | 4-Cl | (CH$_2$)$_4$ |
| 3.394 | 2,4-Cl$_2$ | (CH$_2$)$_4$ |
| 3.395 | 2,6-Cl$_2$ | (CH$_2$)$_4$ |
| 3.396 | 2-F | (CH$_2$)$_4$ |
| 3.397 | 4-F | (CH$_2$)$_4$ |
| 3.398 | 2,4-F$_2$ | (CH$_2$)$_4$ |
| 3.399 | 2,6-F$_2$ | (CH$_2$)$_4$ |
| 3.400 | 4-Br | (CH$_2$)$_4$ |
| 3.401 | 4-NO$_2$ | (CH$_2$)$_4$ |
| 3.402 | 4-OMe | (CH$_2$)$_4$ |
| 3.403 | 4-SMe | (CH$_2$)$_4$ |
| 3.404 | 4-SO$_2$Me | (CH$_2$)$_4$ |
| 3.405 | 4-OCHF$_2$ | (CH$_2$)$_4$ |
| 3.406 | 4-OCF$_3$ | (CH$_2$)$_4$ |
| 3.407 | 4-Ph | (CH$_2$)$_4$ |
| 3.408 | 4-OPh | (CH$_2$)$_4$ |
| 3.409 | 4-OCH$_2$Ph | (CH$_2$)$_4$ |

TABLE 3-continued

| | | |
|---|---|---|
| 3.410 | 4-CH=CH—Ph | (CH$_2$)$_4$ |
| 3.411 | 4-NH$_2$ | (CH$_2$)$_4$ |
| 3.412 | 4-OCO$_2$Et | (CH$_2$)$_4$ |
| 3.413 | 4-NHCO$_2$Et | (CH$_2$)$_4$ |
| 3.414 | 4-CO$_2$Et | (CH$_2$)$_4$ |
| 3.415 | 4-CONMe$_2$ | (CH$_2$)$_4$ |
| 3.416 | H | CH(Me)CH(Me) |
| 3.417 | 2-Me | CH(Me)CH(Me) |
| 3.418 | 4-Me | CH(Me)CH(Me) |
| 3.419 | 4-Et | CH(Me)CH(Me) |
| 3.420 | 4-t-Bu | CH(Me)CH(Me) |
| 3.421 | 2,4-Me$_2$ | CH(Me)CH(Me) |
| 3.422 | 2,6-Me$_2$ | CH(Me)CH(Me) |
| 3.423 | 3,4-Me$_2$ | CH(Me)CH(Me) |
| 3.424 | 4-CF$_3$ | CH(Me)CH(Me) |
| 3.425 | 2-Cl | CH(Me)CH(Me) |
| 3.426 | 4-Cl | CH(Me)CH(Me) |
| 3.427 | 2,4-Cl$_2$ | CH(Me)CH(Me) |
| 3.428 | 2,6-Cl$_2$ | CH(Me)CH(Me) |
| 3.429 | 2-F | CH(Me)CH(Me) |
| 3.430 | 4-F | CH(Me)CH(Me) |
| 3.431 | 2,4-F$_2$ | CH(Me)CH(Me) |
| 3.432 | 2,6-F$_2$ | CH(Me)CH(Me) |
| 3.433 | 4-Br | CH(Me)CH(Me) |
| 3.434 | 4-NO$_2$ | CH(Me)CH(Me) |
| 3.435 | 4-OMe | CH(Me)CH(Me) |
| 3.436 | 4-SMe | CH(Me)CH(Me) |
| 3.437 | 4-SO$_2$Me | CH(Me)CH(Me) |
| 3.438 | 4-OCHF$_2$ | CH(Me)CH(Me) |
| 3.439 | 4-OCF$_3$ | CH(Me)CH(Me) |
| 3.440 | 4-Ph | CH(Me)CH(Me) |
| 3.441 | 4-OPh | CH(Me)CH(Me) |
| 3.442 | 4-OCH$_2$Ph | CH(Me)CH(Me) |
| 3.443 | 4-CH=CH—Ph | CH(Me)CH(Me) |
| 3.444 | 4-NH$_2$ | CH(Me)CH(Me) |
| 3.445 | 4-OCO$_2$Et | CH(Me)CH(Me) |
| 3.446 | 4-NHCO$_2$Et | CH(Me)CH(Me) |
| 3.447 | 4-CO$_2$Et | CH(Me)CH(Me) |
| 3.448 | 4-CONMe$_2$ | CH(Me)CH(Me) |
| 3.449 | H | CH$_2$C(Me)$_2$ |
| 3.450 | 2-Me | CH$_2$C(Me)$_2$ |
| 3.451 | 4-Me | CH$_2$C(Me)$_2$ |
| 3.452 | 4-Et | CH$_2$C(Me)$_2$ |
| 3.453 | 4-t-Bu | CH$_2$C(Me)$_2$ |
| 3.454 | 2,4-Me$_2$ | CH$_2$C(Me)$_2$ |
| 3.455 | 2,6-Me$_2$ | CH$_2$C(Me)$_2$ |
| 3.456 | 3,4-Me$_2$ | CH$_2$C(Me)$_2$ |
| 3.457 | 4-CF$_3$ | CH$_2$C(Me)$_2$ |
| 3.458 | 2-Cl | CH$_2$C(Me)$_2$ |
| 3.459 | 4-Cl | CH$_2$C(Me)$_2$ |
| 3.460 | 2,4-Cl$_2$ | CH$_2$C(Me)$_2$ |
| 3.461 | 2,6-Cl$_2$ | CH$_2$C(Me)$_2$ |
| 3.462 | 2-F | CH$_2$C(Me)$_2$ |
| 3.463 | 4-F | CH$_2$C(Me)$_2$ |
| 3.464 | 2,4-F$_2$ | CH$_2$C(Me)$_2$ |
| 3.465 | 2,6-F$_2$ | CH$_2$C(Me)$_2$ |
| 3.466 | 4-Br | CH$_2$C(Me)$_2$ |
| 3.467 | 4-NO$_2$ | CH$_2$C(Me)$_2$ |
| 3.468 | 4-OMe | CH$_2$C(Me)$_2$ |
| 3.469 | 4-SMe | CH$_2$C(Me)$_2$ |
| 3.470 | 4-SO$_2$Me | CH$_2$C(Me)$_2$ |
| 3.471 | 4-OCHF$_2$ | CH$_2$C(Me)$_2$ |
| 3.472 | 4-OCF$_3$ | CH$_2$C(Me)$_2$ |
| 3.473 | 4-Ph | CH$_2$C(Me)$_2$ |
| 3.474 | 4-OPh | CH$_2$C(Me)$_2$ |
| 3.475 | 4-OCH$_2$Ph | CH$_2$C(Me)$_2$ |
| 3.476 | 4-CH=CH—Ph | CH$_2$C(Me)$_2$ |
| 3.477 | 4-NH$_2$ | CH$_2$C(Me)$_2$ |
| 3.478 | 4-OCO$_2$Et | CH$_2$C(Me)$_2$ |
| 3.479 | 4-NHCO$_2$Et | CH$_2$C(Me)$_2$ |
| 3.480 | 4-CO$_2$Et | CH$_2$C(Me)$_2$ |
| 3.481 | 4-CONMe$_2$ | CH$_2$C(Me)$_2$ |
| 3.482 | H | CH$_2$C(Me)$_2$CH$_2$ |
| 3.483 | 2-Me | CH$_2$C(Me)$_2$CH$_2$ |
| 3.484 | 4-Me | CH$_2$C(Me)$_2$CH$_2$ |
| 3.485 | 4-Et | CH$_2$C(Me)$_2$CH$_2$ |
| 3.486 | 4-t-Bu | CH$_2$C(Me)$_2$CH$_2$ |
| 3.487 | 2,4-Me$_2$ | CH$_2$C(Me)$_2$CH$_2$ |
| 3.488 | 2,6-Me$_2$ | CH$_2$C(Me)$_2$CH$_2$ |
| 3.489 | 3,4-Me$_2$ | CH$_2$C(Me)$_2$CH$_2$ |
| 3.490 | 4-CF$_3$ | CH$_2$C(Me)$_2$CH$_2$ |
| 3.491 | 2-Cl | CH$_2$C(Me)$_2$CH$_2$ |
| 3.492 | 4-Cl | CH$_2$C(Me)$_2$CH$_2$ |
| 3.493 | 2,4-Cl$_2$ | CH$_2$C(Me)$_2$CH$_2$ |
| 3.494 | 2,6-Cl$_2$ | CH$_2$C(Me)$_2$CH$_2$ |
| 3.495 | 2-F | CH$_2$C(Me)$_2$CH$_2$ |
| 3.496 | 4-F | CH$_2$C(Me)$_2$CH$_2$ |
| 3.497 | 2,4-F$_2$ | CH$_2$C(Me)$_2$CH$_2$ |
| 3.498 | 2,6-F$_2$ | CH$_2$C(Me)$_2$CH$_2$ |
| 3.499 | 4-Br | CH$_2$C(Me)$_2$CH$_2$ |
| 3.500 | 4-NO$_2$ | CH$_2$C(Me)$_2$CH$_2$ |
| 3.501 | 4-OMe | CH$_2$C(Me)$_2$CH$_2$ |
| 3.502 | 4-SMe | CH$_2$C(Me)$_2$CH$_2$ |
| 3.503 | 4-SO$_2$Me | CH$_2$C(Me)$_2$CH$_2$ |
| 3.504 | 4-OCHF$_2$ | CH$_2$C(Me)$_2$CH$_2$ |
| 3.505 | 4-OCF$_3$ | CH$_2$C(Me)$_2$CH$_2$ |
| 3.506 | 4-Ph | CH$_2$C(Me)$_2$CH$_2$ |
| 3.507 | 4-OPh | CH$_2$C(Me)$_2$CH$_2$ |
| 3.508 | 4-OCH$_2$Ph | CH$_2$C(Me)$_2$CH$_2$ |
| 3.509 | 4-CH=CH—Ph | CH$_2$C(Me)$_2$CH$_2$ |
| 3.510 | 4-NH$_2$ | CH$_2$C(Me)$_2$CH$_2$ |
| 3.511 | 4-OCO$_2$Et | CH$_2$C(Me)$_2$CH$_2$ |
| 3.512 | 4-NHCO$_2$Et | CH$_2$C(Me)$_2$CH$_2$ |
| 3.513 | 4-CO$_2$Et | CH$_2$C(Me)$_2$CH$_2$ |
| 3.514 | 4-CONMe$_2$ | CH$_2$C(Me)$_2$CH$_2$ |
| 3.515 | H | CH$_2$CH=CH |
| 3.516 | 2-Me | CH$_2$CH=CH |
| 3.517 | 4-Me | CH$_2$CH=CH |
| 3.518 | 4-Et | CH$_2$CH=CH |
| 3.519 | 4-t-Bu | CH$_2$CH=CH |
| 3.520 | 2,4-Me$_2$ | CH$_2$CH=CH |
| 3.521 | 2,6-Me$_2$ | CH$_2$CH=CH |
| 3.522 | 3,4-Me$_2$ | CH$_2$CH=CH |
| 3.523 | 4-CF$_3$ | CH$_2$CH=CH |
| 3.524 | 2-Cl | CH$_2$CH=CH |
| 3.525 | 4-Cl | CH$_2$CH=CH |
| 3.526 | 2,4-Cl$_2$ | CH$_2$CH=CH |
| 3.527 | 2,6-Cl$_2$ | CH$_2$CH=CH |
| 3.528 | 2-F | CH$_2$CH=CH |
| 3.529 | 4-F | CH$_2$CH=CH |
| 3.530 | 2,4-F$_2$ | CH$_2$CH=CH |
| 3.531 | 2,6-F$_2$ | CH$_2$CH=CH |
| 3.532 | 4-Br | CH$_2$CH=CH |
| 3.533 | 4-NO$_2$ | CH$_2$CH=CH |
| 3.534 | 4-OMe | CH$_2$CH=CH |
| 3.535 | 4-SMe | CH$_2$CH=CH |
| 3.536 | 4-SO$_2$Me | CH$_2$CH=CH |
| 3.537 | 4-OCHF$_2$ | CH$_2$CH=CH |
| 3.538 | 4-OCF$_3$ | CH$_2$CH=CH |
| 3.539 | 4-Ph | CH$_2$CH=CH |
| 3.540 | 4-OPh | CH$_2$CH=CH |
| 3.541 | 4-OCH$_2$Ph | CH$_2$CH=CH |
| 3.542 | 4-CH=CH—Ph | CH$_2$CH=CH |
| 3.543 | 4-NH$_2$ | CH$_2$CH=CH |
| 3.544 | 4-OCO$_2$Et | CH$_2$CH=CH |
| 3.545 | 4-NHCO$_2$Et | CH$_2$CH=CH |
| 3.546 | 4-CO$_2$Et | CH$_2$CH=CH |
| 3.547 | 4-CONMe$_2$ | CH$_2$CH=CH |
| 3.548 | H | CH(Me)CH=CH |
| 3.549 | 2-Me | CH(Me)CH=CH |
| 3.550 | 4-Me | CH(Me)CH=CH |
| 3.551 | 4-Et | CH(Me)CH=CH |
| 3.552 | 4-t-Bu | CH(Me)CH=CH |
| 3.553 | 2,4-Me$_2$ | CH(Me)CH=CH |
| 3.554 | 2,6-Me$_2$ | CH(Me)CH=CH |
| 3.555 | 3,4-Me$_2$ | CH(Me)CH=CH |
| 3.556 | 4-CF$_3$ | CH(Me)CH=CH |
| 3.557 | 2-Cl | CH(Me)CH=CH |
| 3.558 | 4-Cl | CH(Me)CH=CH |
| 3.559 | 2,4-Cl$_2$ | CH(Me)CH=CH |
| 3.560 | 2,6-Cl$_2$ | CH(Me)CH=CH |
| 3.561 | 2-F | CH(Me)CH=CH |
| 3.562 | 4-F | CH(Me)CH=CH |
| 3.563 | 2,4-F$_2$ | CH(Me)CH=CH |
| 3.564 | 2,6-F$_2$ | CH(Me)CH=CH |
| 3.565 | 4-Br | CH(Me)CH=CH |
| 3.566 | 4-NO$_2$ | CH(Me)CH=CH |
| 3.567 | 4-OMe | CH(Me)CH=CH |

TABLE 3-continued

| | | |
|---|---|---|
| 3.568 | 4-SMe | CH(Me)CH=CH |
| 3.569 | 4-SO₂Me | CH(Me)CH=CH |
| 3.570 | 4-OCHF₂ | CH(Me)CH=CH |
| 3.571 | 4-OCF₃ | CH(Me)CH=CH |
| 3.572 | 4-Ph | CH(Me)CH=CH |
| 3.573 | 4-OPh | CH(Me)CH=CH |
| 3.574 | 4-OCH₂Ph | CH(Me)CH=CH |
| 3.575 | 4-CH=CH—Ph | CH(Me)CH=CH |
| 3.576 | 4-NH₂ | CH(Me)CH=CH |
| 3.577 | 4-OCO₂Et | CH(Me)CH=CH |
| 3.578 | 4-NHCO₂Et | CH(Me)CH=CH |
| 3.579 | 4-CO₂Et | CH(Me)CH=CH |
| 3.580 | 4-CONMe₂ | CH(Me)CH=CH |
| 3.581 | H | CH₂C(Me)=CH |
| 3.582 | 2-Me | CH₂C(Me)=CH |
| 3.583 | 4-Me | CH₂C(Me)=CH |
| 3.584 | 4-Et | CH₂C(Me)=CH |
| 3.585 | 4-t-Bu | CH₂C(Me)=CH |
| 3.586 | 2,4-Me₂ | CH₂C(Me)=CH |
| 3.587 | 2,6-Me₂ | CH₂C(Me)=CH |
| 3.588 | 3,4-Me₂ | CH₂C(Me)=CH |
| 3.589 | 4-CF₃ | CH₂C(Me)=CH |
| 3.590 | 2-Cl | CH₂C(Me)=CH |
| 3.591 | 4-Cl | CH₂C(Me)=CH |
| 3.592 | 2,4-Cl₂ | CH₂C(Me)=CH |
| 3.593 | 2,6-Cl₂ | CH₂C(Me)=CH |
| 3.594 | 2-F | CH₂C(Me)=CH |
| 3.595 | 4-F | CH₂C(Me)=CH |
| 3.596 | 2,4-F₂ | CH₂C(Me)=CH |
| 3.597 | 2,6-F₂ | CH₂C(Me)=CH |
| 3.598 | 4-Br | CH₂C(Me)=CH |
| 3.599 | 4-NO₂ | CH₂C(Me)=CH |
| 3.600 | 4-OMe | CH₂C(Me)=CH |
| 3.601 | 4-SMe | CH₂C(Me)=CH |
| 3.602 | 4-SO₂Me | CH₂C(Me)=CH |
| 3.603 | 4-OCHF₂ | CH₂C(Me)=CH |
| 3.604 | 4-OCF₃ | CH₂C(Me)=CH |
| 3.605 | 4-Ph | CH₂C(Me)=CH |
| 3.606 | 4-OPh | CH₂C(Me)=CH |
| 3.607 | 4-OCH₂Ph | CH₂C(Me)=CH |
| 3.608 | 4-CH=CH—Ph | CH₂C(Me)=CH |
| 3.609 | 4-NH₂ | CH₂C(Me)=CH |
| 3.610 | 4-OCO₂Et | CH₂C(Me)=CH |
| 3.611 | 4-NHCO₂Et | CH₂C(Me)=CH |
| 3.612 | 4-CO₂Et | CH₂C(Me)=CH |
| 3.613 | 4-CONMe₂ | CH₂C(Me)=CH |
| 3.614 | H | CH₂CH=C(Me) |
| 3.615 | 2-Me | CH₂CH=C(Me) |
| 3.616 | 4-Me | CH₂CH=C(Me) |
| 3.617 | 4-Et | CH₂CH=C(Me) |
| 3.618 | 4-t-Bu | CH₂CH=C(Me) |
| 3.619 | 2,4-Me₂ | CH₂CH=C(Me) |
| 3.620 | 2,6-Me₂ | CH₂CH=C(Me) |
| 3.621 | 3,4-Me₂ | CH₂CH=C(Me) |
| 3.622 | 4-CF₃ | CH₂CH=C(Me) |
| 3.623 | 2-Cl | CH₂CH=C(Me) |
| 3.624 | 4-Cl | CH₂CH=C(Me) |
| 3.625 | 2,4-Cl₂ | CH₂CH=C(Me) |
| 3.626 | 2,6-Cl₂ | CH₂CH=C(Me) |
| 3.627 | 2-F | CH₂CH=C(Me) |
| 3.628 | 4-F | CH₂CH=C(Me) |
| 3.629 | 2,4-F₂ | CH₂CH=C(Me) |
| 3.630 | 2,6-F₂ | CH₂CH=C(Me) |
| 3.631 | 4-Br | CH₂CH=C(Me) |
| 3.632 | 4-NO₂ | CH₂CH=C(Me) |
| 3.633 | 4-OMe | CH₂CH=C(Me) |
| 3.634 | 4-SMe | CH₂CH=C(Me) |
| 3.635 | 4-SO₂Me | CH₂CH=C(Me) |
| 3.636 | 4-OCHF₂ | CH₂CH=C(Me) |
| 3.637 | 4-OCF₃ | CH₂CH=C(Me) |
| 3.638 | 4-Ph | CH₂CH=C(Me) |
| 3.639 | 4-OPh | CH₂CH=C(Me) |
| 3.640 | 4-OCH₂Ph | CH₂CH=C(Me) |
| 3.641 | 4-CH=CH—Ph | CH₂CH=C(Me) |
| 3.642 | 4-NH₂ | CH₂CH=C(Me) |
| 3.643 | 4-OCO₂Et | CH₂CH=C(Me) |
| 3.644 | 4-NHCO₂Et | CH₂CH=C(Me) |
| 3.645 | 4-CO₂Et | CH₂CH=C(Me) |
| 3.646 | 4-CONMe₂ | CH₂CH=C(Me) |

TABLE 3-continued

| | | |
|---|---|---|
| 3.647 | H | (CH₂)₂O |
| 3.648 | 2-Me | (CH₂)₂O |
| 3.649 | 3-Me | (CH₂)₂O |
| 3.650 | 4-Me | (CH₂)₂O |
| 3.651 | 2-Et | (CH₂)₂O |
| 3.652 | 3-Et | (CH₂)₂O |
| 3.653 | 4-Et | (CH₂)₂O |
| 3.654 | 2-Pr | (CH₂)₂O |
| 3.655 | 3-Pr | (CH₂)₂O |
| 3.656 | 4-Pr | (CH₂)₂O |
| 3.657 | 2-i-Pr | (CH₂)₂O |
| 3.658 | 3-i-Pr | (CH₂)₂O |
| 3.659 | 4-i-Pr | (CH₂)₂O |
| 3.660 | 2-t-Bu | (CH₂)₂O |
| 3.661 | 3-t-Bu | (CH₂)₂O |
| 3.662 | 4-t-Bu | (CH₂)₂O |
| 3.663 | 2,4-Me₂ | (CH₂)₂O |
| 3.664 | 2,5-Me₂ | (CH₂)₂O |
| 3.665 | 2,6-Me₂ | (CH₂)₂O |
| 3.666 | 3,4-Me₂ | (CH₂)₂O |
| 3.667 | 2,4,6-Me₃ | (CH₂)₂O |
| 3.668 | 4-t-Bu-2,6-Me₂ | (CH₂)₂O |
| 3.669 | 3,5-(t-Bu)₂-4-OH | (CH₂)₂O |
| 3.670 | 2-CF₃ | (CH₂)₂O |
| 3.671 | 3-CF₃ | (CH₂)₂O |
| 3.672 | 4-CF₃ | (CH₂)₂O |
| 3.673 | 2-Cl | (CH₂)₂O |
| 3.674 | 3-Cl | (CH₂)₂O |
| 3.675 | 4-Cl | (CH₂)₂O |
| 3.676 | 2,4-Cl₂ | (CH₂)₂O |
| 3.677 | 2,5-Cl₂ | (CH₂)₂O |
| 3.678 | 2,6-Cl₂ | (CH₂)₂O |
| 3.679 | 3,4-Cl₂ | (CH₂)₂O |
| 3.680 | 2,4,6-Cl₃ | (CH₂)₂O |
| 3.681 | 2-F | (CH₂)₂O |
| 3.682 | 3-F | (CH₂)₂O |
| 3.683 | 4-F | (CH₂)₂O |
| 3.684 | 2,4-F₂ | (CH₂)₂O |
| 3.685 | 3,4-F₂ | (CH₂)₂O |
| 3.686 | 2,6-F₂ | (CH₂)₂O |
| 3.687 | 2-Br | (CH₂)₂O |
| 3.688 | 3-Br | (CH₂)₂O |
| 3.689 | 4-Br | (CH₂)₂O |
| 3.690 | 2,4-Br₂ | (CH₂)₂O |
| 3.691 | 2,6-Br₂ | (CH₂)₂O |
| 3.692 | 3,4-Br₂ | (CH₂)₂O |
| 3.693 | 4-I | (CH₂)₂O |
| 3.694 | 4-Cl-2-Me | (CH₂)₂O |
| 3.695 | 2-NO₂ | (CH₂)₂O |
| 3.696 | 3-NO₂ | (CH₂)₂O |
| 3.697 | 4-NO₂ | (CH₂)₂O |
| 3.698 | 2-Cl-4-NO₂ | (CH₂)₂O |
| 3.699 | 3-Cl-4-NO₂ | (CH₂)₂O |
| 3.700 | 4-Cl-3-NO₂ | (CH₂)₂O |
| 3.701 | 4-OH | (CH₂)₂O |
| 3.702 | 2-OMe | (CH₂)₂O |
| 3.703 | 3-OMe | (CH₂)₂O |
| 3.704 | 4-OMe | (CH₂)₂O |
| 3.705 | 4-OBu | (CH₂)₂O |
| 3.706 | 3,4-(OMe)₂ | (CH₂)₂O |
| 3.707 | 4-SMe | (CH₂)₂O |
| 3.708 | 4-SOMe | (CH₂)₂O |
| 3.709 | 4-SO₂Me | (CH₂)₂O |
| 3.710 | 4-OCHF₂ | (CH₂)₂O |
| 3.711 | 4-OCF₃ | (CH₂)₂O |
| 3.712 | 2-Ph | (CH₂)₂O |
| 3.713 | 3-Ph | (CH₂)₂O |
| 3.714 | 4-Ph | (CH₂)₂O |
| 3.715 | 2-OPh | (CH₂)₂O |
| 3.716 | 3-OPh | (CH₂)₂O |
| 3.717 | 4-OPh | (CH₂)₂O |
| 3.718 | 2-OCH₂Ph | (CH₂)₂O |
| 3.719 | 3-OCH₂Ph | (CH₂)₂O |
| 3.720 | 4-OCH₂Ph | (CH₂)₂O |
| 3.721 | 4-CH=CH—Ph | (CH₂)₂O |
| 3.722 | 4-NH₂ | (CH₂)₂O |
| 3.723 | 4-NMe₂ | (CH₂)₂O |
| 3.724 | 4-OCO₂Me | (CH₂)₂O |
| 3.725 | 4-OCO₂Et | (CH₂)₂O |

TABLE 3-continued

| | | |
|---|---|---|
| 3.726 | 4-OCO$_2$t-Bu | (CH$_2$)$_2$O |
| 3.727 | 3-Cl-4-OCO$_2$t-Bu | (CH$_2$)$_2$O |
| 3.728 | 4-NHCO$_2$Me | (CH$_2$)$_2$O |
| 3.729 | 4-NHCO$_2$Et | (CH$_2$)$_2$O |
| 3.730 | 4-NHCO$_2$t-Bu | (CH$_2$)$_2$O |
| 3.731 | 4-CO$_2$Me | (CH$_2$)$_2$O |
| 3.732 | 4-CO$_2$Et | (CH$_2$)$_2$O |
| 3.733 | 4-CONHMe | (CH$_2$)$_2$O |
| 3.734 | 4-CONHEt | (CH$_2$)$_2$O |
| 3.735 | 4-CONMe$_2$ | (CH$_2$)$_2$O |
| 3.736 | 4-CONEt$_2$ | (CH$_2$)$_2$O |
| 3.737 | H | (CH$_2$)$_3$O |
| 3.738 | 2-Me | (CH$_2$)$_3$O |
| 3.739 | 3-Me | (CH$_2$)$_3$O |
| 3.740 | 4-Me | (CH$_2$)$_3$O |
| 3.741 | 4-Et | (CH$_2$)$_3$O |
| 3.742 | 4-i-Pr | (CH$_2$)$_3$O |
| 3.743 | 4-t-Bu | (CH$_2$)$_3$O |
| 3.744 | 2,4-Me$_2$ | (CH$_2$)$_3$O |
| 3.745 | 2,6-Me$_2$ | (CH$_2$)$_3$O |
| 3.746 | 3,4-Me$_2$ | (CH$_2$)$_3$O |
| 3.747 | 4-CF$_3$ | (CH$_2$)$_3$O |
| 3.748 | 2-Cl | (CH$_2$)$_3$O |
| 3.749 | 3-Cl | (CH$_2$)$_3$O |
| 3.750 | 4-Cl | (CH$_2$)$_3$O |
| 3.751 | 2,4-Cl$_2$ | (CH$_2$)$_3$O |
| 3.752 | 2,6-Cl$_2$ | (CH$_2$)$_3$O |
| 3.753 | 2-F | (CH$_2$)$_3$O |
| 3.754 | 3-F | (CH$_2$)$_3$O |
| 3.755 | 4-F | (CH$_2$)$_3$O |
| 3.756 | 2,4-F$_2$ | (CH$_2$)$_3$O |
| 3.757 | 2,6-F$_2$ | (CH$_2$)$_3$O |
| 3.758 | 4-Br | (CH$_2$)$_3$O |
| 3.759 | 2,4-Br$_2$ | (CH$_2$)$_3$O |
| 3.760 | 4-I | (CH$_2$)$_3$O |
| 3.761 | 4-NO$_2$ | (CH$_2$)$_3$O |
| 3.762 | 4-OMe | (CH$_2$)$_3$O |
| 3.763 | 3,4-(OMe)$_2$ | (CH$_2$)$_3$O |
| 3.764 | 4-SMe | (CH$_2$)$_3$O |
| 3.765 | 4-SO$_2$Me | (CH$_2$)$_3$O |
| 3.766 | 4-OCHF$_2$ | (CH$_2$)$_3$O |
| 3.767 | 4-OCF$_3$ | (CH$_2$)$_3$O |
| 3.768 | 4-Ph | (CH$_2$)$_3$O |
| 3.769 | 2-OPh | (CH$_2$)$_3$O |
| 3.770 | 3-OPh | (CH$_2$)$_3$O |
| 3.771 | 4-OPh | (CH$_2$)$_3$O |
| 3.772 | 2-OCH$_2$Ph | (CH$_2$)$_3$O |
| 3.773 | 3-OCH$_2$Ph | (CH$_2$)$_3$O |
| 3.774 | 4-OCH$_2$Ph | (CH$_2$)$_3$O |
| 3.775 | 4-CH=CH—Ph | (CH$_2$)$_3$O |
| 3.776 | 4-NH$_2$ | (CH$_2$)$_3$O |
| 3.777 | 4-OCO$_2$Et | (CH$_2$)$_3$O |
| 3.778 | 4-NHCO$_2$Et | (CH$_2$)$_3$O |
| 3.779 | 4-CO$_2$Et | (CH$_2$)$_3$O |
| 3.780 | 4-CONMe$_2$ | (CH$_2$)$_3$O |

TABLE 4

In the compounds of

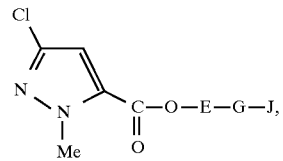

(a)

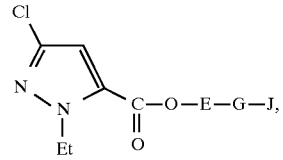

(b)

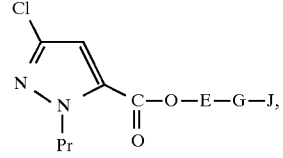

(c)

TABLE 4-continued (d) 5-Cl, 1-iPr pyrazole-C(=O)-O-E-G-J (e) 5-Cl, 1-Bu pyrazole-C(=O)-O-E-G-J (f) 5-Cl, 1-tBu pyrazole-C(=O)-O-E-G-J or (g) 5-Br, 1-Me pyrazole-C(=O)-O-E-G-J

| Compound No. | E | G | J |
| --- | --- | --- | --- |
| 4.1 | H | — | — |
| 4.2 | Me | — | — |
| 4.3 | Et | — | — |
| 4.4 | Pr | — | — |
| 4.5 | i-Pr | — | — |
| 4.6 | Bu | — | — |
| 4.7 | s-Bu | — | — |
| 4.8 | i-Bu | — | — |
| 4.9 | t-Bu | — | — |
| 4.10 | Pen | — | — |
| 4.11 | $CH(Me)CH_2CH_2CH_3$ | — | — |
| 4.12 | $CH_2CH(Me)CH_2CH_3$ | — | — |
| 4.13 | $(CH_2)_2CH(Me)_2$ | — | — |
| 4.14 | $CH_2C(Me)_3$ | — | — |
| 4.15 | Hex | — | — |
| 4.16 | $CH(Me)C(Me)_3$ | — | — |
| 4.17 | cyc-Pr | — | — |
| 4.18 | $CH_2$cyc-Pr | — | — |
| 4.19 | $CH_2(1\text{-}CH_3\text{-cyc-Pr})$ | — | — |
| 4.20 | cyc-Bu | — | — |
| 4.21 | cyc-Pen | — | — |
| 4.22 | cyc-Hex | — | — |
| 4.23 | $CH_2$cyc-Hex | — | — |
| 4.24 | $(CH_2)_2$cyc-Hex | — | — |
| 4.25 | (4-t-Bu)-cyc-Hex | — | — |
| 4.26 | (4-Ph)-cyc-Hex | — | — |
| 4.27 | $CH_2CH=CH_2$ | — | — |
| 4.28 | $(CH_2)_2CH=CH_2$ | — | — |
| 4.29 | $CH(Me)CH=CH_2$ | — | — |
| 4.30 | $CH_2C(Me)=CH_2$ | — | — |
| 4.31 | $CH_2CH=CHMe$ | — | — |
| 4.32 | $C(Me)_2CH=CH_2$ | — | — |
| 4.33 | $CH_2C(Me)=CHMe$ | — | — |

TABLE 4-continued

| | | | |
|---|---|---|---|
| 4.34 | $CH_2CH=C(Me)_2$ | — | — |
| 4.35 | $(CH_2)_3CH=CH_2$ | — | — |
| 4.36 | $CH_2C(Me)=C(Me)_2$ | — | — |
| 4.37 | $CH_2C\equiv CH$ | — | — |
| 4.38 | $CH(Me)C\equiv CH$ | — | — |
| 4.39 | $C(Me)_2C\equiv CH$ | — | — |
| 4.40 | $CH_2C\equiv CMe$ | — | — |
| 4.41 | $(CH_2)_2C\equiv CEt$ | — | — |
| 4.42 | $(CH_2)_2Cl$ | — | — |
| 4.43 | $(CH_2)_2Br$ | — | — |
| 4.44 | $(CH_2)_2I$ | — | — |
| 4.45 | $(CH_2)_2F$ | — | — |
| 4.46 | $CH_2CHCl_2$ | — | — |
| 4.47 | $CH_2CHBr_2$ | — | — |
| 4.48 | $CH_2CHF_2$ | — | — |
| 4.49 | $CH_2CCl_3$ | — | — |
| 4.50 | $CH_2CBr_3$ | — | — |
| 4.51 | $CH_2CF_3$ | — | — |
| 4.52 | $(CH_2)_3Cl$ | — | — |
| 4.53 | $(CH_2)_3Br$ | — | — |
| 4.54 | $(CH_2)_3F$ | — | — |
| 4.55 | $CH_2CHClCH_2Cl$ | — | — |
| 4.56 | $CH_2CHBrCH_2Br$ | — | — |
| 4.57 | $CH_2CHFCH_2F$ | — | — |
| 4.58 | $CH(CH_2Cl)_2$ | — | — |
| 4.59 | $CH(CH_2Br)_2$ | — | — |
| 4.60 | $CH(CH_2F)_2$ | — | — |
| 4.61 | $CH_2C(Cl)=CH_2$ | — | — |
| 4.62 | $CH_2CH=CHCl$ | — | — |
| 4.63 | $CH_2CH=CCl_2$ | — | — |
| 4.64 | $CH_2C(Cl)=CHCl$ | — | — |
| 4.65 | $CH_2COMe$ | — | — |
| 4.66 | $CH_2COPh$ | — | — |
| 4.67 | $(CH_2)_2COMe$ | — | — |
| 4.68 | $(CH_2)_2COPh$ | — | — |
| 4.69 | $CH(CO_2Me)_2$ | — | — |
| 4.70 | $CH(CO_2Et)_2$ | — | — |
| 4.71 | $CH(CN)CO_2Me$ | — | — |
| 4.72 | $CH(COMe)CO_2Me$ | — | — |
| 4.73 | $CH(Ph)_2$ | — | — |
| 4.74 | $CH_2CH(PH)_2$ | — | — |
| 4.75 | $W_1$ | — | — |
| 4.76 | $W_2$ | — | — |
| 4.77 | $W_3$ | — | — |
| 4.78 | $W_4$ | — | — |
| 4.79 | $W_5$ | — | — |
| 4.80 | $W_6$ | — | — |
| 4.81 | $W_7$ | — | — |
| 4.82 | $W_8$ | — | — |
| 4.83 | $W_9$ | — | — |
| 4.84 | $W_{10}$ | — | — |
| 4.85 | $W_{11}$ | — | — |
| 4.86 | $W_{12}$ | — | — |
| 4.87 | $W_{13}$ | — | — |
| 4.88 | $W_{14}$ | — | — |
| 4.89 | $W_{15}$ | — | — |
| 4.90 | $W_{16}$ | — | — |
| 4.91 | $W_{17}$ | — | — |
| 4.92 | $W_{18}$ | — | — |
| 4.93 | $W_{19}$ | — | — |
| 4.94 | $W_{20}$ | — | — |
| 4.95 | $CH_2$ | CN | — |
| 4.96 | $(CH_2)_2$ | CN | — |
| 4.97 | $CH(Me)$ | CN | — |
| 4.98 | $(CH_2)_3$ | CN | — |
| 4.99 | $CH_2CH(Me)$ | CN | — |
| 4.100 | $CH(Me)CH_2$ | CN | — |
| 4.101 | $(CH_2)_4$ | CN | — |
| 4.102 | $CH(Me)CH(Me)$ | CN | — |
| 4.103 | $CH_2C(Me)_2$ | CN | — |
| 4.104 | $CH_2C(Me)_2CH_2$ | CN | — |
| 4.105 | $CH_2$ | O | Me |
| 4.106 | $CH_2$ | O | Et |
| 4.107 | $CH_2$ | O | Pr |

TABLE 4-continued

| | | | |
|---|---|---|---|
| 4.108 | $CH_2$ | O | i-Pr |
| 4.109 | $CH_2$ | O | Bu |
| 4.110 | $CH_2$ | O | s-Bu |
| 4.111 | $CH_2$ | O | i-Bu |
| 4.112 | $CH_2$ | O | t-Bu |
| 4.113 | $CH_2$ | O | Pen |
| 4.114 | $CH_2$ | O | Hex |
| 4.115 | $CH_2$ | O | cyc-Pr |
| 4.116 | $CH_2$ | O | cyc-Bu |
| 4.117 | $CH_2$ | O | cyc-Pen |
| 4.118 | $CH_2$ | O | cyc-Hex |
| 4.119 | $CH_2$ | O | $CH_2CCl_3$ |
| 4.120 | $CH_2$ | O | $CH_2CBr_3$ |
| 4.121 | $CH_2$ | O | $CH_2CF_3$ |
| 4.122 | $CH_2$ | O | $CH_2Ph$ |
| 4.123 | $CH_2$ | O | $(CH_2)_2OMe$ |
| 4.124 | $CH_2$ | O | $(CH_2)_2OEt$ |
| 4.125 | $(CH_2)_2$ | O | H |
| 4.126 | $(CH_2)_2$ | O | Me |
| 4.127 | $(CH_2)_2$ | O | Et |
| 4.128 | $(CH_2)_2$ | O | Pr |
| 4.129 | $(CH_2)_2$ | O | i-Pr |
| 4.130 | $(CH_2)_2$ | O | Bu |
| 4.131 | $(CH_2)_2$ | O | s-Bu |
| 4.132 | $(CH_2)_2$ | O | i-Bu |
| 4.133 | $(CH_2)_2$ | O | t-Bu |
| 4.134 | $(CH_2)_2$ | O | Pen |
| 4.135 | $(CH_2)_2$ | O | $CH(Me)CH_2CH_2CH_3$ |
| 4.136 | $(CH_2)_2$ | O | $CH_2CH(Me)CH_2CH_3$ |
| 4.137 | $(CH_2)_2$ | O | $(CH_2)_2CH(Me)_2$ |
| 4.138 | $(CH_2)_2$ | O | $CH_2C(Me)_3$ |
| 4.139 | $(CH_2)_2$ | O | Hex |
| 4.140 | $(CH_2)_2$ | O | cyc-Pr |
| 4.141 | $(CH_2)_2$ | O | cyc-Bu |
| 4.142 | $(CH_2)_2$ | O | cyc-Pen |
| 4.143 | $(CH_2)_2$ | O | cyc-Hex |
| 4.144 | $(CH_2)_2$ | O | $CH_2CH=CH_2$ |
| 4.145 | $(CH_2)_2$ | O | $(CH_2)_2CH=CH_2$ |
| 4.146 | $(CH_2)_2$ | O | $CH(Me)CH=CH_2$ |
| 4.147 | $(CH_2)_2$ | O | $CH_2C(Me)=CH_2$ |
| 4.148 | $(CH_2)_2$ | O | $CH_2CH=CHMe$ |
| 4.149 | $(CH_2)_2$ | O | $C(Me)_2CH=CH_2$ |
| 4.150 | $(CH_2)_2$ | O | $CH_2C(Me)=CHMe$ |
| 4.151 | $(CH_2)_2$ | O | $CH_2CH=C(Me)_2$ |
| 4.152 | $(CH_2)_2$ | O | $(CH_2)_3CH=CH_2$ |
| 4.153 | $(CH_2)_2$ | O | $CH_2C(Me)=C(Me)_2$ |
| 4.154 | $(CH_2)_2$ | O | $CH_2C\equiv CH$ |
| 4.155 | $(CH_2)_2$ | O | $CH(Me)C\equiv CH$ |
| 4.156 | $(CH_2)_2$ | O | $C(Me)_2C\equiv CH$ |
| 4.157 | $(CH_2)_2$ | O | $CH_2C\equiv CMe$ |
| 4.158 | $(CH_2)_2$ | O | $CH_2C\equiv CEt$ |
| 4.159 | $(CH_2)_2$ | O | $(CH_2)_2Cl$ |
| 4.160 | $(CH_2)_2$ | O | $(CH_2)_2Br$ |
| 4.161 | $(CH_2)_2$ | O | $(CH_2)_2I$ |
| 4.162 | $(CH_2)_2$ | O | $(CH_2)_2F$ |
| 4.163 | $(CH_2)_2$ | O | $CH_2CHCl_2$ |
| 4.164 | $(CH_2)_2$ | O | $CH_2CHBr_2$ |
| 4.165 | $(CH_2)_2$ | O | $CH_2CHF_2$ |
| 4.166 | $(CH_2)_2$ | O | $CH_2CCl_3$ |
| 4.167 | $(CH_2)_2$ | O | $CH_2CBr_3$ |
| 4.168 | $(CH_2)_2$ | O | $CH_2CF_3$ |
| 4.169 | $(CH_2)_2$ | O | $(CH_2)_3Cl$ |
| 4.170 | $(CH_2)_2$ | O | $(CH_2)_3Br$ |
| 4.171 | $(CH_2)_2$ | O | $(CH_2)_3F$ |
| 4.172 | $(CH_2)_2$ | O | $CH_2CHClCH_2Cl$ |
| 4.173 | $(CH_2)_2$ | O | $CH_2CHBrCH_2Br$ |
| 4.174 | $(CH_2)_2$ | O | $CH_2CHFCH_2F$ |
| 4.175 | $(CH_2)_2$ | O | $CH(CH_2Cl)_2$ |
| 4.176 | $(CH_2)_2$ | O | $CH(CH_2Br)_2$ |
| 4.177 | $(CH_2)_2$ | O | $CH(CH_2F)_2$ |
| 4.178 | $(CH_2)_2$ | O | $CH_2C(Cl)=CH_2$ |
| 4.179 | $(CH_2)_2$ | O | $CH_2CH=CHCl$ |
| 4.180 | $(CH_2)_2$ | O | $CH_2CH=CCl_2$ |
| 4.181 | $(CH_2)_2$ | O | $CH_2C(Cl)=CHCl$ |

TABLE 4-continued

| | | | |
|---|---|---|---|
| 4.182 | (CH$_2$)$_2$ | O | CH$_2$Ph |
| 4.183 | (CH$_2$)$_2$ | O | CH$_2$COMe |
| 4.184 | (CH$_2$)$_2$ | O | CH$_2$COPh |
| 4.185 | (CH$_2$)$_2$ | O | (CH$_2$)$_2$COMe |
| 4.186 | (CH$_2$)$_2$ | O | (CH$_2$)$_2$NMe$_2$ |
| 4.187 | (CH$_2$)$_2$ | O | CONHMe |
| 4.188 | (CH$_2$)$_2$ | O | (CH$_2$)$_2$OMe |
| 4.189 | (CH$_2$)$_2$ | O | (CH$_2$)$_2$OEt |
| 4.190 | (CH$_2$)$_2$ | O | (CH$_2$)$_2$OPr |
| 4.191 | (CH$_2$)$_2$ | O | (CH$_2$)$_2$OBu |
| 4.192 | (CH$_2$)$_2$ | O | (CH$_2$)$_2$Ot-Bu |
| 4.193 | (CH$_2$)$_2$ | O | (CH$_2$)$_2$OCH$_2$CH=CH$_2$ |
| 4.194 | (CH$_2$)$_2$ | O | (CH$_2$)$_2$OCH$_2$C≡CH |
| 4.195 | (CH$_2$)$_2$ | O | (CH$_2$)$_2$O(CH$_2$)$_2$Cl |
| 4.196 | (CH$_2$)$_2$ | O | (CH$_2$)$_2$OPh |
| 4.197 | (CH$_2$)$_2$ | O | W$_{21}$ |
| 4.198 | CH(Me) | O | Me |
| 4.199 | CH(Me) | O | Et |
| 4.200 | CH(Me) | O | Pr |
| 4.201 | CH(Me) | O | Bu |
| 4.202 | (CH$_2$)$_3$ | O | H |
| 4.203 | (CH$_2$)$_3$ | O | Me |
| 4.204 | (CH$_2$)$_3$ | O | Et |
| 4.205 | (CH$_2$)$_3$ | O | Pr |
| 4.206 | (CH$_2$)$_3$ | O | i-Pr |
| 4.207 | (CH$_2$)$_3$ | O | Bu |
| 4.208 | (CH$_2$)$_3$ | O | s-Bu |
| 4.209 | (CH$_2$)$_3$ | O | i-Bu |
| 4.210 | (CH$_2$)$_3$ | O | t-Bu |
| 4.211 | (CH$_2$)$_3$ | O | Pen |
| 4.212 | (CH$_2$)$_3$ | O | CH(Me)CH$_2$CH$_2$CH$_3$ |
| 4.213 | (CH$_2$)$_3$ | O | CH$_2$CH(Me)CH$_2$CH$_3$ |
| 4.214 | (CH$_2$)$_3$ | O | (CH$_2$)$_2$CH(Me)$_2$ |
| 4.215 | (CH$_2$)$_3$ | O | CH$_2$C(Me)$_3$ |
| 4.216 | (CH$_2$)$_3$ | O | Hex |
| 4.217 | (CH$_2$)$_3$ | O | cyc-Pr |
| 4.218 | (CH$_2$)$_3$ | O | cyc-Bu |
| 4.219 | (CH$_2$)$_3$ | O | cyc-Pen |
| 4.220 | (CH$_2$)$_3$ | O | cyc-Hex |
| 4.221 | (CH$_2$)$_3$ | O | CH$_2$CH=CH$_2$ |
| 4.222 | (CH$_2$)$_3$ | O | (CH$_2$)$_2$CH=CH$_2$ |
| 4.223 | (CH$_2$)$_3$ | O | CH(Me)CH=CH$_2$ |
| 4.224 | (CH$_2$)$_3$ | O | CH$_2$C(Me)=CH$_2$ |
| 4.225 | (CH$_2$)$_3$ | O | CH$_2$CH=CHMe |
| 4.226 | (CH$_2$)$_3$ | O | CH$_2$C≡CH |
| 4.227 | (CH$_2$)$_3$ | O | CH(Me)C≡CH |
| 4.228 | (CH$_2$)$_3$ | O | CH$_2$C≡CMe |
| 4.229 | (CH$_2$)$_3$ | O | (CH$_2$)$_2$Cl |
| 4.230 | (CH$_2$)$_3$ | O | CH$_2$CHCl$_2$ |
| 4.231 | (CH$_2$)$_3$ | O | CH$_2$CCl$_3$ |
| 4.232 | CH$_2$CH(Me) | O | H |
| 4.233 | CH$_2$CH(Me) | O | Me |
| 4.234 | CH$_2$CH(Me) | O | Et |
| 4.235 | CH$_2$CH(Me) | O | Pr |
| 4.236 | CH$_2$CH(Me) | O | i-Pr |
| 4.237 | CH$_2$CH(Me) | O | Bu |
| 4.238 | CH$_2$CH(Me) | O | s-Bu |
| 4.239 | CH$_2$CH(Me) | O | i-Bu |
| 4.240 | CH$_2$CH(Me) | O | t-Bu |
| 4.241 | CH$_2$CH(Me) | O | Pen |
| 4.242 | CH$_2$CH(Me) | O | Hex |
| 4.243 | CH$_2$CH(Me) | O | CH$_2$CH=CH$_2$ |
| 4.244 | CH$_2$CH(Me) | O | CH$_2$C≡CH |
| 4.245 | CH$_2$CH(Me) | O | (CH$_2$)$_2$Cl |
| 4.246 | CH$_2$CH(Me) | O | CH$_2$CHCl$_2$ |
| 4.247 | CH$_2$CH(Me) | O | CH$_2$CCl$_3$ |
| 4.248 | CH(Me)CH$_2$ | O | H |
| 4.249 | CH(Me)CH$_2$ | O | Me |
| 4.250 | CH(Me)CH$_2$ | O | Et |
| 4.251 | CH(Me)CH$_2$ | O | Pr |
| 4.252 | CH(Me)CH$_2$ | O | i-Pr |
| 4.253 | CH(Me)CH$_2$ | O | Bu |
| 4.254 | CH(Me)CH$_2$ | O | s-Bu |
| 4.255 | CH(Me)CH$_2$ | O | i-Bu |

TABLE 4-continued

| | | | |
|---|---|---|---|
| 4.256 | CH(Me)CH$_2$ | O | t-Bu |
| 4.257 | CH(Me)CH$_2$ | O | Pen |
| 4.258 | CH(Me)CH$_2$ | O | Hex |
| 4.259 | CH(Me)CH$_2$ | O | CH$_2$CH=CH$_2$ |
| 4.260 | CH(Me)CH$_2$ | O | CH$_2$C≡CH |
| 4.261 | CH(Me)CH$_2$ | O | (CH$_2$)$_2$Cl |
| 4.262 | CH(Me)CH$_2$ | O | CH$_2$CHCl$_2$ |
| 4.263 | CH(Me)CH$_2$ | O | CH$_2$CCl$_3$ |
| 4.264 | (CH$_2$)$_4$ | O | H |
| 4.265 | (CH$_2$)$_4$ | O | Me |
| 4.266 | (CH$_2$)$_4$ | O | Et |
| 4.267 | (CH$_2$)$_4$ | O | Pr |
| 4.268 | (CH$_2$)$_4$ | O | i-Pr |
| 4.269 | (CH$_2$)$_4$ | O | Bu |
| 4.270 | (CH$_2$)$_4$ | O | s-Bu |
| 4.271 | (CH$_2$)$_4$ | O | i-Bu |
| 4.272 | (CH$_2$)$_4$ | O | t-Bu |
| 4.273 | (CH$_2$)$_4$ | O | Pen |
| 4.274 | (CH$_2$)$_4$ | O | Hex |
| 4.275 | (CH$_2$)$_4$ | O | CH$_2$CH=CH$_2$ |
| 4.276 | (CH$_2$)$_4$ | O | CH$_2$C≡CH |
| 4.277 | (CH$_2$)$_4$ | O | (CH$_2$)$_2$Cl |
| 4.278 | (CH$_2$)$_4$ | O | CH$_2$CHCl$_2$ |
| 4.279 | (CH$_2$)$_4$ | O | CH$_2$CCl$_3$ |
| 4.280 | CH(Me)CH(Me) | O | H |
| 4.281 | CH(Me)CH(Me) | O | Me |
| 4.282 | CH(Me)CH(Me) | O | Et |
| 4.283 | CH(Me)CH(Me) | O | Pr |
| 4.284 | CH(Me)CH(Me) | O | i-Pr |
| 4.285 | CH(Me)CH(Me) | O | Bu |
| 4.286 | CH(Me)CH(Me) | O | s-Bu |
| 4.287 | CH(Me)CH(Me) | O | i-Bu |
| 4.288 | CH(Me)CH(Me) | O | t-Bu |
| 4.289 | CH(Me)CH(Me) | O | Pen |
| 4.290 | CH(Me)CH(Me) | O | Hex |
| 4.291 | CH(Me)CH(Me) | O | CH$_2$CH=CH$_2$ |
| 4.292 | CH(Me)CH(Me) | O | CH$_2$C≡CH |
| 4.293 | CH(Me)CH(Me) | O | (CH$_2$)$_2$Cl |
| 4.294 | CH(Me)CH(Me) | O | CH$_2$CHCl$_2$ |
| 4.295 | CH(Me)CH(Me) | O | CH$_2$CCl$_3$ |
| 4.296 | CH$_2$ | CO$_2$ | H |
| 4.297 | CH$_2$ | CO$_2$ | Me |
| 4.298 | CH$_2$ | CO$_2$ | Et |
| 4.299 | CH$_2$ | CO$_2$ | Pr |
| 4.300 | CH$_2$ | CO$_2$ | i-Pr |
| 4.301 | CH$_2$ | CO$_2$ | Bu |
| 4.302 | CH$_2$ | CO$_2$ | s-Bu |
| 4.303 | CH$_2$ | CO$_2$ | i-Bu |
| 4.304 | CH$_2$ | CO$_2$ | t-Bu |
| 4.305 | CH$_2$ | CO$_2$ | Pen |
| 4.306 | CH$_2$ | CO$_2$ | CH(Me)CH$_2$CH$_2$CH$_3$ |
| 4.307 | CH$_2$ | CO$_2$ | CH$_2$CH(Me)CH$_2$CH$_3$ |
| 4.308 | CH$_2$ | CO$_2$ | (CH$_2$)$_2$CH(Me)$_2$ |
| 4.309 | CH$_2$ | CO$_2$ | CH$_2$C(Me)$_3$ |
| 4.310 | CH$_2$ | CO$_2$ | Hex |
| 4.311 | CH$_2$ | CO$_2$ | CH(Me)C(Me)$_3$ |
| 4.312 | CH$_2$ | CO$_2$ | cyc-Pr |
| 4.313 | CH$_2$ | CO$_2$ | CH$_2$cyc-Pr |
| 4.314 | CH$_2$ | CO$_2$ | CH$_2$(1-CH$_3$-cyc-Pr) |
| 4.315 | CH$_2$ | CO$_2$ | cyc-Bu |
| 4.316 | CH$_2$ | CO$_2$ | cyc-Pen |
| 4.317 | CH$_2$ | CO$_2$ | cyc-Hex |
| 4.318 | CH$_2$ | CO$_2$ | CH$_2$cyc-Hex |
| 4.319 | CH$_2$ | CO$_2$ | (CH$_2$)$_2$cyc-Hex |
| 4.320 | CH$_2$ | CO$_2$ | CH$_2$CH=CH$_2$ |
| 4.321 | CH$_2$ | CO$_2$ | (CH$_2$)$_2$CH=CH$_2$ |
| 4.322 | CH$_2$ | CO$_2$ | CH(Me)CH=CH$_2$ |
| 4.323 | CH$_2$ | CO$_2$ | CH$_2$C(Me)=CH$_2$ |
| 4.324 | CH$_2$ | CO$_2$ | CH$_2$CH=CHMe |
| 4.325 | CH$_2$ | CO$_2$ | C(Me)$_2$CH=CH$_2$ |
| 4.326 | CH$_2$ | CO$_2$ | CH$_2$C(Me)=CHMe |
| 4.327 | CH$_2$ | CO$_2$ | CH$_2$CH=C(Me)$_2$ |
| 4.328 | CH$_2$ | CO$_2$ | (CH$_2$)$_3$CH=CH$_2$ |
| 4.329 | CH$_2$ | CO$_2$ | CH$_2$C(Me)=C(Me)$_2$ |
| 4.330 | CH$_2$ | CO$_2$ | CH$_2$C≡CH |

TABLE 4-continued

| | | | |
|---|---|---|---|
| 4.331 | $CH_2$ | $CO_2$ | $CH(Me)C\equiv CH$ |
| 4.332 | $CH_2$ | $CO_2$ | $C(Me)_2C\equiv CH$ |
| 4.333 | $CH_2$ | $CO_2$ | $CH_2C\equiv CMe$ |
| 4.334 | $CH_2$ | $CO_2$ | $CH_2C\equiv CEt$ |
| 4.335 | $CH_2$ | $CO_2$ | $(CH_2)_2Cl$ |
| 4.336 | $CH_2$ | $CO_2$ | $(CH_2)_2Br$ |
| 4.337 | $CH_2$ | $CO_2$ | $(CH_2)_2I$ |
| 4.338 | $CH_2$ | $CO_2$ | $(CH_2)_2F$ |
| 4.339 | $CH_2$ | $CO_2$ | $CH_2CHCl_2$ |
| 4.340 | $CH_2$ | $CO_2$ | $CH_2CHBr_2$ |
| 4.341 | $CH_2$ | $CO_2$ | $CH_2CHF_2$ |
| 4.342 | $CH_2$ | $CO_2$ | $CH_2CCl_3$ |
| 4.343 | $CH_2$ | $CO_2$ | $CH_2CBr_3$ |
| 4.344 | $CH_2$ | $CO_2$ | $CH_2CF_3$ |
| 4.345 | $CH_2$ | $CO_2$ | $(CH_2)_3Cl$ |
| 4.346 | $CH_2$ | $CO_2$ | $(CH_2)_3Br$ |
| 4.347 | $CH_2$ | $CO_2$ | $(CH_2)_3F$ |
| 4.348 | $CH_2$ | $CO_2$ | $CH_2CHClCH_2Cl$ |
| 4.349 | $CH_2$ | $CO_2$ | $CH_2CHBrCH_2Br$ |
| 4.350 | $CH_2$ | $CO_2$ | $CH_2CHFCH_2F$ |
| 4.351 | $CH_2$ | $CO_2$ | $CH_2C(Cl)=CH_2$ |
| 4.352 | $CH_2$ | $CO_2$ | $CH_2CH=CHCl$ |
| 4.353 | $CH_2$ | $CO_2$ | $CH_2CH=CCl_2$ |
| 4.354 | $CH_2$ | $CO_2$ | $CH_2C(Cl)=CHCl$ |
| 4.355 | $CH_2$ | $CO_2$ | $CH_2COMe$ |
| 4.356 | $CH_2$ | $CO_2$ | $CH_2COPh$ |
| 4.357 | $CH_2$ | $CO_2$ | $(CH_2)_2COMe$ |
| 4.358 | $CH_2$ | $CO_2$ | $(CH_2)_2COPh$ |
| 4.359 | $CH_2$ | $CO_2$ | $W_1$ |
| 4.360 | $CH_2$ | $CO_2$ | $W_2$ |
| 4.361 | $CH_2$ | $CO_2$ | $W_3$ |
| 4.362 | $CH_2$ | $CO_2$ | $W_4$ |
| 4.363 | $CH(Me)$ | $CO_2$ | H |
| 4.364 | $CH(Me)$ | $CO_2$ | Me |
| 4.365 | $CH(Me)$ | $CO_2$ | Et |
| 4.366 | $CH(Me)$ | $CO_2$ | Pr |
| 4.367 | $CH(Me)$ | $CO_2$ | i-Pr |
| 4.368 | $CH(Me)$ | $CO_2$ | Bu |
| 4.369 | $CH(Me)$ | $CO_2$ | s-Bu |
| 4.370 | $CH(Me)$ | $CO_2$ | i-Bu |
| 4.371 | $CH(Me)$ | $CO_2$ | t-Bu |
| 4.372 | $CH(Me)$ | $CO_2$ | Pen |
| 4.373 | $CH(Me)$ | $CO_2$ | $CH(Me)CH_2CH_2CH_3$ |
| 4.374 | $CH(Me)$ | $CO_2$ | $CH_2CH(Me)CH_2CH_3$ |
| 4.375 | $CH(Me)$ | $CO_2$ | $(CH_2)_2CH(Me)_2$ |
| 4.376 | $CH(Me)$ | $CO_2$ | $CH_2C(Me)_3$ |
| 4.377 | $CH(Me)$ | $CO_2$ | Hex |
| 4.378 | $CH(Me)$ | $CO_2$ | $CH(Me)C(Me)_3$ |
| 4.379 | $CH(Me)$ | $CO_2$ | cyc-Pr |
| 4.380 | $CH(Me)$ | $CO_2$ | $CH_2$cyc-Pr |
| 4.381 | $CH(Me)$ | $CO_2$ | $CH_2(1\text{-}CH_3\text{-cyc-Pr})$ |
| 4.382 | $CH(Me)$ | $CO_2$ | cyc-Bu |
| 4.383 | $CH(Me)$ | $CO_2$ | cyc-Pen |
| 4.384 | $CH(Me)$ | $CO_2$ | cyc-Hex |
| 4.385 | $CH(Me)$ | $CO_2$ | $CH_2$cyc-Hex |
| 4.386 | $CH(Me)$ | $CO_2$ | $(CH_2)_2$cyc-Hex |
| 4.387 | $CH(Me)$ | $CO_2$ | $CH_2CH=CH_2$ |
| 4.388 | $CH(Me)$ | $CO_2$ | $(CH_2)_2CH=CH_2$ |
| 4.389 | $CH(Me)$ | $CO_2$ | $CH(Me)CH=CH_2$ |
| 4.390 | $CH(Me)$ | $CO_2$ | $CH_2C(Me)=CH_2$ |
| 4.391 | $CH(Me)$ | $CO_2$ | $CH_2CH=CHMe$ |
| 4.392 | $CH(Me)$ | $CO_2$ | $C(Me)_2CH=CH_2$ |
| 4.393 | $CH(Me)$ | $CO_2$ | $CH_2C(Me)=CHMe$ |
| 4.394 | $CH(Me)$ | $CO_2$ | $CH_2CH=C(Me)_2$ |
| 4.395 | $CH(Me)$ | $CO_2$ | $(CH_2)_3CH=CH_2$ |
| 4.396 | $CH(Me)$ | $CO_2$ | $CH_2C(Me)=C(Me)_2$ |
| 4.397 | $CH(Me)$ | $CO_2$ | $CH_2C\equiv CH$ |
| 4.398 | $CH(Me)$ | $CO_2$ | $CH(Me)C\equiv CH$ |
| 4.399 | $CH(Me)$ | $CO_2$ | $C(Me)_2C\equiv CH$ |
| 4.400 | $CH(Me)$ | $CO_2$ | $CH_2C\equiv CMe$ |
| 4.401 | $CH(Me)$ | $CO_2$ | $CH_2C\equiv CEt$ |

TABLE 4-continued

| | | | |
|---|---|---|---|
| 4.402 | CH(Me) | $CO_2$ | $(CH_2)_2Cl$ |
| 4.403 | CH(Me) | $CO_2$ | $(CH_2)_2Br$ |
| 4.404 | CH(Me) | $CO_2$ | $(CH_2)_2I$ |
| 4.405 | CH(Me) | $CO_2$ | $(CH_2)_2F$ |
| 4.406 | CH(Me) | $CO_2$ | $CH_2CHCl_2$ |
| 4.407 | CH(Me) | $CO_2$ | $CH_2CHBr_2$ |
| 4.408 | CH(Me) | $CO_2$ | $CH_2CHF_2$ |
| 4.409 | CH(Me) | $CO_2$ | $CH_2CCl_3$ |
| 4.410 | CH(Me) | $CO_2$ | $CH_2CBr_3$ |
| 4.411 | CH(Me) | $CO_2$ | $CH_2CF_3$ |
| 4.412 | CH(Me) | $CO_2$ | $(CH_2)_3Cl$ |
| 4.413 | CH(Me) | $CO_2$ | $(CH_2)_3Br$ |
| 4.414 | CH(Me) | $CO_2$ | $(CH_2)_3F$ |
| 4.415 | CH(Me) | $CO_2$ | $CH_2CHClCH_2Cl$ |
| 4.416 | CH(Me) | $CO_2$ | $CH_2CHBrCH_2Br$ |
| 4.417 | CH(Me) | $CO_2$ | $CH_2CHFCH_2F$ |
| 4.418 | CH(Me) | $CO_2$ | $CH_2C(Cl)=CH_2$ |
| 4.419 | CH(Me) | $CO_2$ | $CH_2CH=CHCl$ |
| 4.420 | CH(Me) | $CO_2$ | $CH_2CH=CCl_2$ |
| 4.421 | CH(Me) | $CO_2$ | $CH_2C(Cl)=CHCl$ |
| 4.422 | $(CH_2)_2$ | $CO_2$ | H |
| 4.423 | $(CH_2)_2$ | $CO_2$ | Me |
| 4.424 | $(CH_2)_2$ | $CO_2$ | Et |
| 4.425 | $(CH_2)_2$ | $CO_2$ | Pr |
| 4.426 | $(CH_2)_2$ | $CO_2$ | i-Pr |
| 4.427 | $(CH_2)_2$ | $CO_2$ | Bu |
| 4.428 | $(CH_2)_2$ | $CO_2$ | Pen |
| 4.429 | $(CH_2)_2$ | $CO_2$ | Hex |
| 4.430 | $(CH_2)_2$ | $CO_2$ | cyc-Pr |
| 4.431 | $(CH_2)_2$ | $CO_2$ | cyc-Bu |
| 4.432 | $(CH_2)_2$ | $CO_2$ | cyc-Pen |
| 4.433 | $(CH_2)_2$ | $CO_2$ | cyc-Hex |
| 4.434 | $(CH_2)_2$ | $CO_2$ | $CH_2CH=CH_2$ |
| 4.435 | $(CH_2)_2$ | $CO_2$ | $CH_2C\equiv CH$ |
| 4.436 | $(CH_2)_2$ | $CO_2$ | $(CH_2)_2Cl$ |
| 4.437 | $(CH_2)_2$ | $CO_2$ | $CH_2CHCl_2$ |
| 4.438 | $(CH_2)_2$ | $CO_2$ | $CH_2CCl_3$ |
| 4.439 | $(CH_2)_3$ | $CO_2$ | H |
| 4.440 | $(CH_2)_3$ | $CO_2$ | Me |
| 4.441 | $(CH_2)_3$ | $CO_2$ | Et |
| 4.442 | $(CH_2)_3$ | $CO_2$ | Pr |
| 4.443 | $(CH_2)_3$ | $CO_2$ | i-Pr |
| 4.444 | $(CH_2)_3$ | $CO_2$ | Bu |
| 4.445 | $(CH_2)_3$ | $CO_2$ | Pen |
| 4.446 | $(CH_2)_3$ | $CO_2$ | Hex |
| 4.447 | $(CH_2)_3$ | $CO_2$ | cyc-Pr |
| 4.448 | $(CH_2)_3$ | $CO_2$ | cyc-Bu |
| 4.449 | $(CH_2)_3$ | $CO_2$ | cyc-Pen |
| 4.450 | $(CH_2)_3$ | $CO_2$ | cyc-Hex |
| 4.451 | $(CH_2)_3$ | $CO_2$ | $CH_2CH=CH_2$ |
| 4.452 | $(CH_2)_3$ | $CO_2$ | $CH_2C\equiv CH$ |
| 4.453 | $(CH_2)_3$ | $CO_2$ | $(CH_2)_2Cl$ |
| 4.454 | $(CH_2)_3$ | $CO_2$ | $CH_2CHCl_2$ |
| 4.455 | $(CH_2)_3$ | $CO_2$ | $CH_2CCl_3$ |
| 4.456 | $CH_2$ | S | H |
| 4.457 | $CH_2$ | S | Me |
| 4.458 | $CH_2$ | S | Et |
| 4.459 | $CH_2$ | S | Pr |
| 4.460 | $(CH_2)_2$ | S | Me |
| 4.461 | $(CH_2)_2$ | S | Et |
| 4.462 | $(CH_2)_2$ | S | Pr |
| 4.463 | $(CH_2)_2$ | S | Bu |
| 4.464 | $(CH_2)_2$ | S | $CH_2CH=CH_2$ |
| 4.465 | $(CH_2)_3$ | S | Me |
| 4.466 | $(CH_2)_3$ | S | Et |
| 4.467 | $(CH_2)_3$ | S | Pr |
| 4.468 | $(CH_2)_3$ | S | Bu |
| 4.469 | $(CH_2)_3$ | S | $CH_2CH=CH_2$ |
| 4.470 | $CH_2$ | SO | Me |
| 4.471 | $CH_2$ | SO | Et |
| 4.472 | $CH_2$ | SO | Pr |
| 4.473 | $CH_2$ | SO | Bu |
| 4.474 | $CH_2$ | SO | $CH_2CH=CH_2$ |
| 4.475 | $(CH_2)_2$ | SO | Me |
| 4.476 | $(CH_2)_2$ | SO | Et |
| 4.477 | $(CH_2)_2$ | SO | Pr |
| 4.478 | $(CH_2)_2$ | SO | Bu |

TABLE 4-continued

| | | | |
|---|---|---|---|
| 4.479 | (CH$_2$)$_2$ | SO | CH$_2$CH=CH$_2$ |
| 4.480 | (CH$_2$)$_3$ | SO | Me |
| 4.481 | (CH$_2$)$_3$ | SO | Et |
| 4.482 | (CH$_2$)$_3$ | SO | Pr |
| 4.483 | (CH$_2$)$_3$ | SO | Bu |
| 4.484 | (CH$_2$)$_3$ | SO | CH$_2$CH=CH$_2$ |
| 4.485 | CH$_2$ | SO$_2$ | Me |
| 4.486 | CH$_2$ | SO$_2$ | Et |
| 4.487 | CH$_2$ | SO$_2$ | Pr |
| 4.488 | CH$_2$ | SO$_2$ | Bu |
| 4.489 | CH$_2$ | SO$_2$ | CH$_2$CH=CH$_2$ |
| 4.490 | (CH$_2$)$_2$ | SO$_2$ | Me |
| 4.491 | (CH$_2$)$_2$ | SO$_2$ | Et |
| 4.492 | (CH$_2$)$_2$ | SO$_2$ | Pr |
| 4.493 | (CH$_2$)$_2$ | SO$_2$ | Bu |
| 4.494 | (CH$_2$)$_2$ | SO$_2$ | CH$_2$CH=CH$_2$ |
| 4.495 | (CH$_2$)$_3$ | SO$_2$ | Me |
| 4.496 | (CH$_2$)$_3$ | SO$_2$ | Et |
| 4.497 | (CH$_2$)$_3$ | SO$_2$ | Pr |
| 4.498 | (CH$_2$)$_3$ | SO$_2$ | Bu |
| 4.499 | (CH$_2$)$_3$ | SO$_2$ | CH$_2$CH=CH$_2$ |

W$_1$–W$_{21}$ in the table 4 show the following structures.

W$_1$:

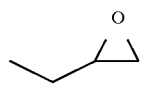

W$_2$:

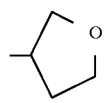

W$_3$:

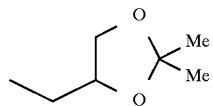

W$_4$:

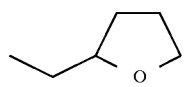

W$_5$:

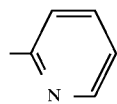

W$_6$:

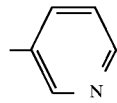

W$_7$:

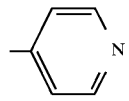

W$_8$:

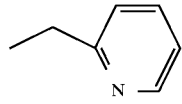

W$_9$:

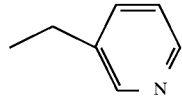

W$_{10}$:

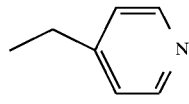

TABLE 4-continued
| | |
|---|---|
| W₁₁: | 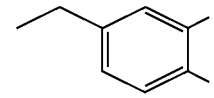 |
| W₁₂: | 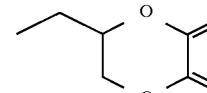 |
| W₁₃: | 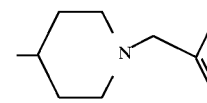 |
| W₁₄: | 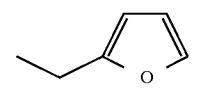 |
| W₁₅: | 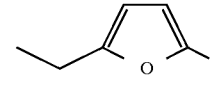 |
| W₁₆: | 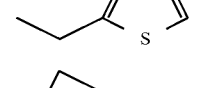 |
| W₁₇: | 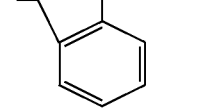 |
| W₁₈: | 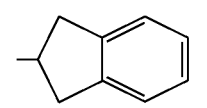 |
| W₁₉: | 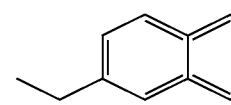 |
| W₂₀: | 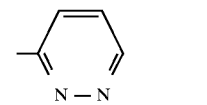 |
| W₂₁: | 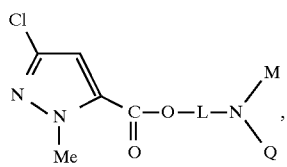 |
TABLE 5
In the compounds of
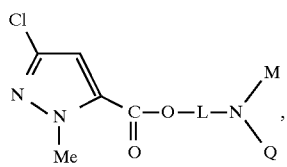
(a)

TABLE 5-continued

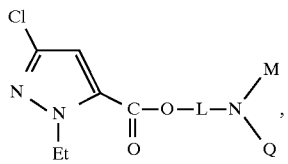

(b)

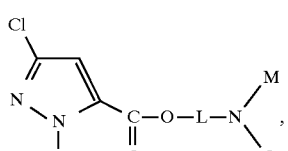

(c)

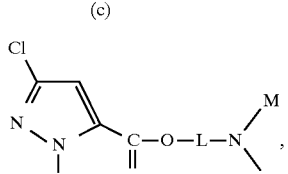

(d)

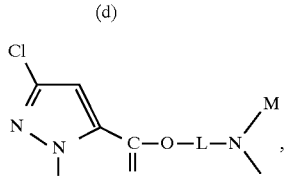

(e)

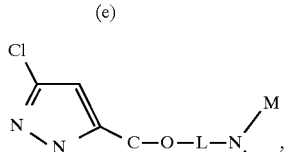

(f)

or

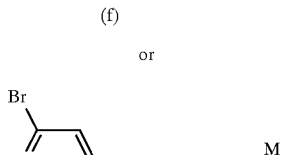

(g)

| Compound No. | L | M | Q |
|---|---|---|---|
| 5.1 | — | H | H |
| 5.2 | — | H | Me |
| 5.3 | — | H | Et |
| 5.4 | — | H | Pr |
| 5.5 | — | H | i-Pr |
| 5.6 | — | H | Bu |
| 5.7 | — | H | t-Bu |
| 5.8 | — | H | CH$_2$CH=CH$_2$ |
| 5.9 | — | H | CH$_2$C≡CH |
| 5.10 | — | H | CH$_2$CH$_2$Cl |
| 5.11 | — | H | CH$_2$CH$_2$F |
| 5.12 | — | H | CH$_2$CH=CHCl |
| 5.13 | — | H | CH$_2$OMe |
| 5.14 | — | H | CH$_2$SMe |
| 5.15 | — | H | CH$_2$Ph |
| 5.16 | — | H | Ph |
| 5.17 | — | H | COMe |
| 5.18 | — | H | COPh |
| 5.19 | — | H | CO$_2$Et |
| 5.20 | — | H | CO$_2$t-Bu |
| 5.21 | — | H | SO$_2$Me |
| 5.22 | — | H | SO$_2$Ph |
| 5.23 | — | Me | Me |
| 5.24 | — | Me | COMe |
| 5.25 | — | Me | COPh |
| 5.26 | — | Me | CO$_2$Et |
| 5.27 | — | Et | Et |
| 5.28 | — | Et | COMe |
| 5.29 | — | Et | COPh |
| 5.30 | (CH$_2$)$_2$ | H | H |
| 5.31 | (CH$_2$)$_2$ | H | Me |
| 5.32 | (CH$_2$)$_2$ | H | Et |
| 5.33 | (CH$_2$)$_2$ | H | Pr |
| 5.34 | (CH$_2$)$_2$ | H | cyc-Pr |
| 5.35 | (CH$_2$)$_2$ | H | CH$_2$Ph |
| 5.36 | (CH$_2$)$_2$ | H | Ph |
| 5.37 | (CH$_2$)$_2$ | H | COMe |
| 5.38 | (CH$_2$)$_2$ | H | COPh |
| 5.39 | (CH$_2$)$_2$ | H | CO$_2$Et |
| 5.40 | (CH$_2$)$_2$ | H | CO$_2$t-Bu |
| 5.41 | (CH$_2$)$_2$ | Me | Me |
| 5.42 | (CH$_2$)$_2$ | Me | Et |
| 5.43 | (CH$_2$)$_2$ | Me | Pr |
| 5.44 | (CH$_2$)$_2$ | Me | CH$_2$Ph |
| 5.45 | (CH$_2$)$_2$ | Me | Ph |
| 5.46 | (CH$_2$)$_2$ | Me | COMe |
| 5.47 | (CH$_2$)$_2$ | Me | COPh |
| 5.48 | (CH$_2$)$_2$ | Me | CO$_2$Et |
| 5.49 | (CH$_2$)$_2$ | Me | CO$_2$t-Bu |
| 5.50 | (CH$_2$)$_2$ | Et | Et |
| 5.51 | (CH$_2$)$_2$ | Et | Pr |
| 5.52 | (CH$_2$)$_2$ | —(CH$_2$)$_4$— | |
| 5.53 | (CH$_2$)$_2$ | —(CH$_2$)$_5$— | |
| 5.54 | (CH$_2$)$_3$ | Me | Me |
| 5.55 | (CH$_2$)$_3$ | Me | Et |
| 5.56 | (CH$_2$)$_3$ | Me | Pr |
| 5.57 | (CH$_2$)$_3$ | Me | CH$_2$Ph |
| 5.58 | (CH$_2$)$_3$ | Me | Ph |
| 5.59 | (CH$_2$)$_3$ | Me | COMe |
| 5.60 | (CH$_2$)$_3$ | Me | COPh |
| 5.61 | (CH$_2$)$_3$ | Me | CO$_2$Et |
| 5.63 | (CH$_2$)$_3$ | Me | CO$_2$t-Bu |
| 5.63 | (CH$_2$)$_3$ | Et | Et |
| 5.64 | (CH$_2$)$_3$ | Et | Pr |
| 5.65 | (CH$_2$)$_3$ | —(CH$_2$)$_4$— | |
| 5.66 | (CH$_2$)$_3$ | —(CH$_2$)$_5$— | |

TABLE 6

In the compounds of

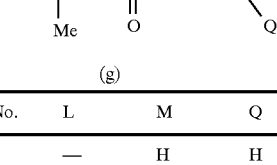

(a)

TABLE 6-continued

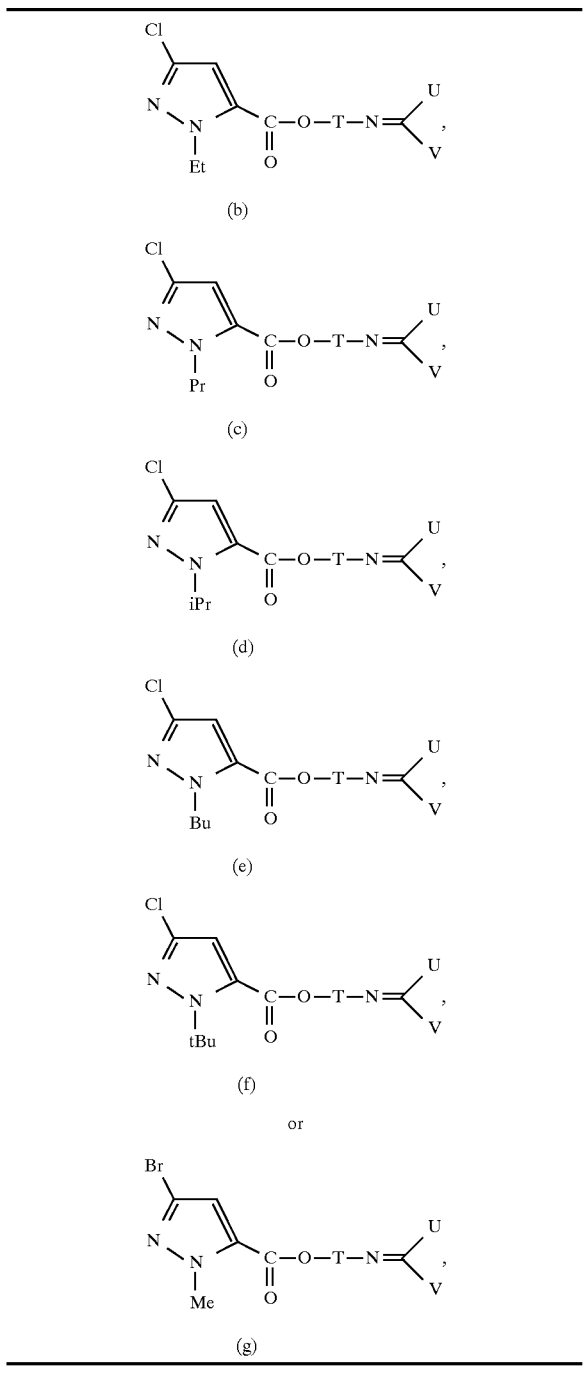

(b), (c), (d), (e), (f)

or (g)

| Compound No. | T | U | V |
|---|---|---|---|
| 6.1 | — | Me | NH$_2$ |
| 6.2 | — | Et | NH$_2$ |
| 6.3 | — | Pr | NH$_2$ |
| 6.4 | — | Bu | NH$_2$ |
| 6.5 | — | t-Bu | NH$_2$ |
| 6.6 | — | Ph | NH$_2$ |
| 6.7 | — | (2-Cl)—Ph | NH$_2$ |
| 6.8 | — | (4-Cl)—Ph | NH$_2$ |
| 6.9 | — | (2-F)—Ph | NH$_2$ |
| 6.10 | — | (4-F)—Ph | NH$_2$ |
| 6.11 | — | CH$_2$Cl | NH$_2$ |
| 6.12 | — | CH$_2$CF$_3$ | NH$_2$ |
| 6.13 | — | Me | NHMe |
| 6.14 | — | Et | NHMe |
| 6.15 | — | Pr | NHMe |
| 6.16 | — | Bu | NHMe |
| 6.17 | — | t-Bu | NHMe |
| 6.18 | — | Ph | NHMe |
| 6.19 | — | (2-Cl)—Ph | NHMe |
| 6.20 | — | (4-Cl)—Ph | NHMe |
| 6.21 | — | (2-F)—Ph | NHMe |
| 6.22 | — | (4-F)—Ph | NHMe |
| 6.23 | — | CH$_2$CCl$_3$ | NHMe |
| 6.24 | — | CH$_2$CF$_3$ | NHMe |
| 6.25 | — | Me | NMe$_2$ |
| 6.26 | — | Et | NMe$_2$ |
| 6.27 | — | Pr | NMe$_2$ |
| 6.28 | — | Bu | NMe$_2$ |
| 6.29 | — | t-Bu | NMe$_2$ |
| 6.30 | — | Ph | NMe$_2$ |
| 6.31 | — | (2-Cl)—Ph | NMe$_2$ |
| 6.32 | — | (4-Cl)—Ph | NMe$_2$ |
| 6.33 | — | (2-F)—Ph | NMe$_2$ |
| 6.34 | — | (4-F)—Ph | NMe$_2$ |
| 6.35 | — | CH$_2$CCl$_3$ | NMe$_2$ |
| 6.36 | — | CH$_2$CF$_3$ | NMe$_2$ |
| 6.37 | (CH$_2$)$_2$O | Me | H |
| 6.38 | (CH$_2$)$_2$O | Me | Me |
| 6.39 | (CH$_2$)$_2$O | Me | t-Bu |
| 6.40 | (CH$_2$)$_2$O | Ph | H |
| 6.41 | (CH$_2$)$_2$O | Ph | Me |

A process for producing the compounds of the present invention is described below. Synthesis of the compound of the formula [1]

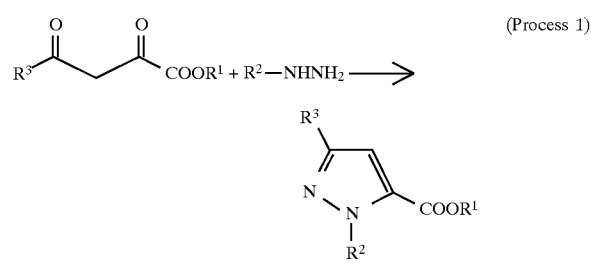

(Process 1)

wherein R$^1$, R$^2$ and R$^3$ have the same meanings as defined above.

(Process 2)

wherein R$^1$, R$^2$ and R$^3$ have the same meanings as defined above, and Z represents a leaving group such as halogen or the like.

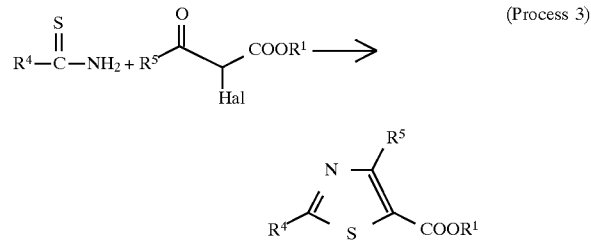

(Process 3)

wherein R$^1$, R$^4$ and R$^5$ have the same meanings as defined above.

(Process 4)

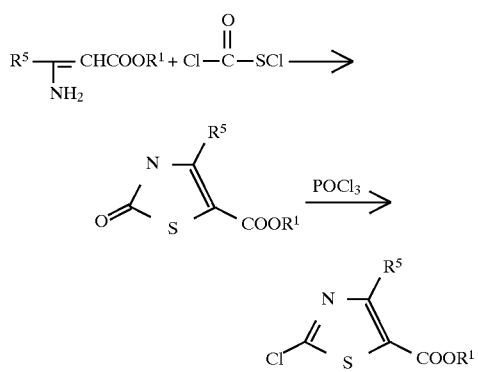

wherein $R^1$ and $R^5$ have the same meanings as defined above.

(Process 5)

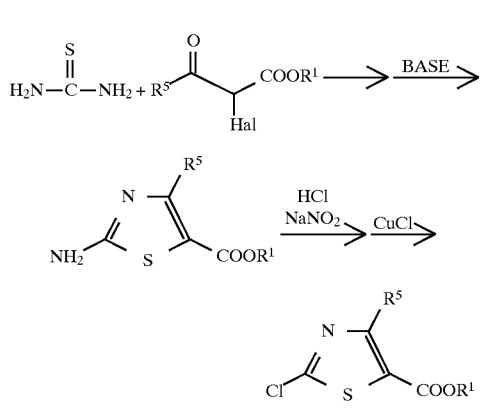

wherein $R^1$ and $R^5$ have the same meanings as defined above.

Synthesis of the compound of the formula [2]

(Process 6)

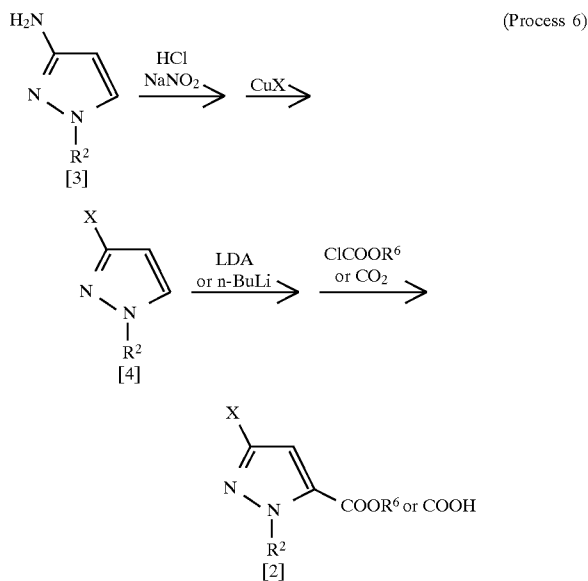

wherein X, $R^2$ and $R^6$ have the same meanings as defined above.

(Process 7)

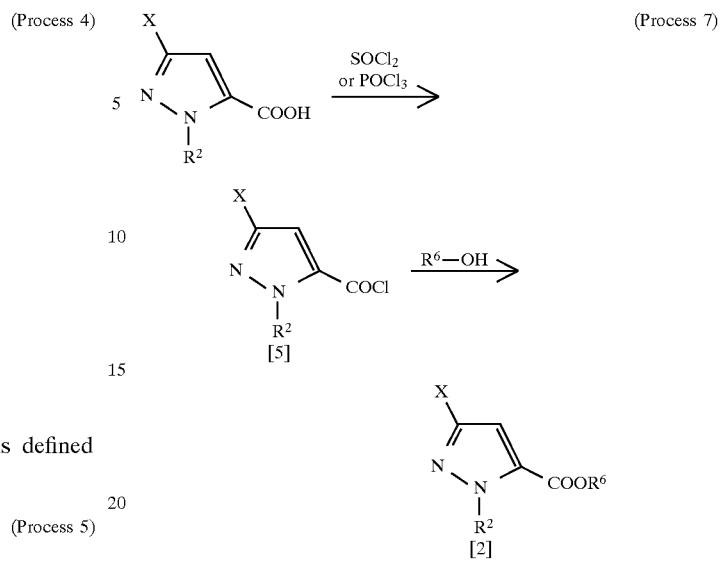

wherein X, $R^2$ and $R^6$ have the same meanings as defined above.

In (Process 1), the compound can be produced by the method reported in Bull. Soc. Chim. Fr., p. 293 (1966) and Chem. Ber. vol. 59, p. 1282 (1926).

In (Process 2), the compound can be produced by the method reported in Chem. Ber., vol. 59, p. 601 (1926) and J. Prak. Chem., vol. 143, p. 259 (1935).

In (Process 3), the compound can be produced by the method reported in Chemical Abstracts, vol. 40, p. 4056 (1946) and J. Chem. Soc., p. 87 (1946).

In (Process 4), the compound can be produced by the method reported in J. Heterocyclic Chem., vol. 22, p. 1621 (1985).

In (Process 5), the compound can be produced by the method reported in Chemical Abstracts, vol. 58, p. 3408 (1963) and Chemical Abstracts, vol. 61, p. 8298 (1964).

A method of producing a novel compound of the formula [2] of (Process 6) is described below.

3-Halogeno-1-alkylpyrazole [4] can be produced by diazotizing 3-amino-1-alkylpyrazole [3] in a usual manner, and adding a copper halide.

It is desirable that the diazotization is normally conducted in a mineral acid such as hydrochloric acid, sulfuric acid or the like at a temperature of from −10° C. to room temperature, preferably from 0° to 10° C. In the reaction with the copper halide, it is possible to directly add the same to a diazonium solution. However, it is desirable to suspend a copper saltin in an inert solvent such as chloroform or the like and add a diazonium solution to the suspension. The reaction is preferably conducted at from 0° to 100° C. or at a reflux temperature of a solvent.

Then, the 5-position of the resulting compound is lithiolized using a lithium compound such as LDA or the like, and the thus-obtained compound is reacted with carbon dioxide gas or a chloroformic acid ester, making it possible to form the intended product [2].

It is usually advisable to conduct the lithiolization and the esterification in an inert solvent such as diethyl ether, THF or the like at a temperature of from −120° C. to room temperature, preferably from −80° C. to 0° C. After the completion of the reaction, the post-treatment is conducted in a usual manner to obtain the intended product.

In (Process 7), the intended product [2] can be formed by converting a 3-halogeno-1-alkyl-5-pyrazolecarboxylic acid in a usual manner into a carbonyl halide [5], and then reacting the same with alcohols.

In the conversion into a carbonyl halide, it is possible to directly add a thionyl halide, a phosphorus halide or the like. It is usually advisable to conduct the conversion in an inert solvent such as chloroform, benzene, toluene or the like at from 0° to 120° C. or at a reflux temperature of a solvent.

The esterification can usually be conducted using an appropriate inert solvent. Examples of the solvent include aromatic hydrocarbons such as toluene, xylene, chlorobenzene and the like; halogenated hydrocarbons such as dichloroethane and the like; ethers such as diisopropyl ether, dioxane and the like; nitrites such as acetonitrile and the like; and polar solvents such as dimethylsulfoxide, dimethylformamide and the like.

An organic base (such as pyridine, triethylamine or the like) or an inorganic base (potassium carbonate, sodium hydroxide or the like) may be added as required.

With respect to the amount of the reagent used in the reaction, an amount of an alcohol is between 1 and 3 equivalents per equivalent of the compound of the formula [5].

Any reaction temperature can be employed in the above-mentioned reaction. However, it is preferably between 0° C. and 50° C.

The plant diseases to be controlled by the compounds of the present invention are as follows.

Rice blast (*Pyricularia oryzae*), Helminthosporium leaft spot (*Cochliobolus miyabeanus*) and Sheat blight (*Rhizoctonia solani*) of paddy.

Powdery mildew (*Erysiphe graminis* f. sp. hordei, f. sp. tritici), Stripe (*Pyrenophora graminea*), Net blotch (*Pyrenophora teres*), Scab and fusarium blight (*Gibberella zeae*), Stripe rust, yellow rust, stem rust, black rust, leaf rust, brown rust and dwarf rust (*Puccinia striiformis, P. graminis, P. recondite, P. hordei*), Snow blight and snow mold (Typhula sp., *Micronectriella nivais*), Loose smut (*Ustilago tritici, U. nuda*), Eyespot (*Pseudocercosporella herpotrichoides*), Scald and leaf blotch (*Rhynchosporium secalis*), Speckled blotch (*Septoria tritici*), and Glume blotch (*Leptosphaeria nodorum*) of barley and wheat, Melanose (*Diaporthe citri*), Scab (*Elsinoe fawcetti*), and Common green mold and blue mold (*Penicillium digitatum, P. italicum*) of fruit trees, Blossom blight (*Sclerotinia mali*), Canker (*Valsa mali*), Powdery mildew (*Podosphaera leucotricha*), Alternaria leaf spot (*Alternaria mali*) and Scab (*Venturia inaequalis*) of apple, Scab (*Venturia nashicola*), Black spot (*Alternaria Kikuchiana*) and Rust (*Gymnosporangium haraeanum*) of pear, Brown rot (*Sclerotinia cinerea*), Scab (*Cladosporium carpophilum*), and Phomopsis rot (*Phomopsis sp.*) of peach, Downy mildew (*Plasmopara viticola*), Anthracnose (*Elsinoe ampelina*), Ripe rot (*Glomerella cingulata*), Powdery mildew (*Uncinula necator*) and Rust (*Phakopsora ampelopsidis*) of grape, Anthracnose (*Gloeosporium kaki*) and Angular leaf spot, and Circular leaf spot (*Cercospora kaki, Mycosphaerella nawae*) of persimmon, Downy mildew (*Pseudoperenospora cubensis*), Anthracnose (*Colletotrichum lagenarium*), Powdery mildew (*Sphaerotheca fuliginea*), and Gummy stem blight (*Mycosphaerella melonis*) of melon, Late blight (*Phytophthora infestans*), Early blight (*Alternaria solani*) and Leaf mold (*Cladosporium fulvam*) of tomato, Brown spot (*Phomopsis vexans*) and Powdery mildew (*Erysiphe cichoracoarum*) of egg plant, Alternaria leaf spot (*Alternaria japonica*) and white spot (*Cerocosporella brassicae*) of vegetable of the family Cruciferae, Rust (*Puccinia allii*) of welsh onion, Purple seed stain (*Cercospora kikuchii*), Sphaceloma scab (*Elsinoe glycines*) and Black spot (*Diaporthe phaseololum*) of soybean, Anthracnose (*Colletotrichum lindemuthianum*) of kidney bean, Leaf spot (*Mycosphaerella personatum*) and Brown leaf spot (*Cercospora arachidicola*) of peanut, Powdery mildew (*Erysiphe pisi*) of garden pea, Early blight (*Alternaria solani*) of potato Powdery mildew (*Sphaerotheca humuli*) of strawberry, Net blister blight (*Exobasidium reticulatum*) and White scab (*Elsinoe leucospila*) of tea, Brown spot (*Alternaria longipes*), Powdery mildew (*Erysiphe cichoracearum*) and Anthracnose (*Colletotrichum tabacum*) of tobacco, Cercospora leaf spot (*Cercospora beticola*) of sugar beat, Black spot (*Diplocarpon rosae*) and Powdery mildew (*Sphaerotheca pannosa*) of rose, Leaf spot (*Septoria chrysanthemiindici*) and Rust (*Puccinia horiana*) of chrysanthemum, Gray mold (*Botrytis cinerea*) of various kinds of crops, and, Sclerotinia rot (*Sclerotinia sclerotiorum*) of various kinds of crops.

When the compound of the present invention is used as an agricultural and horticultural microbicide, it can generally be mixed with an appropriate carrier. Examples of the carrier include solid carriers such as clay, talc, bentonite, diatomaceous earth and the like; and liquid carriers such as water, alcohols (such as methanol, ethanol and the like), aromatic hydrocarbons (such as benzene, toluene, xylene and the like), chlorinated hydrocarbons, ethers, ketones, esters (such as ethyl acetate and the like), acid amides (such as dimethylformamide and the like) and the like. An emulsifier, a dispersing agent, a suspending agent, a penetrating agent, a spreader, a stabilizer and the like can be added thereto as required. The compound of the present inventipractical use to practical use in any form of a liquid preparation, an emulsifiable concentrate, a wettable powder, a dust, a granule, a flowable or the like.

When the compounds of the present invention are used as an agricultural and horticultural microbicide, it can be applied through foliar application, soil treatment, seed disinfection or the like. A general method which is used by those skilled in the art is also available. The compounds of the present invention may be applied, as required, in combination with preparations or other herbicides, insecticides, disinfectants, plant growth regulators, synergists and the like at the time of the application. The dose of the compounds in the present invention varies depending on an application place, an application time, an application method, diseases to be treated, cultivation crops and the like. In general, it is between approximately 0.005 kg and 50 kg per hectare.

Formulation examples of fungicides comprising the compounds of the present invention as the active ingredient are mentioned hereiunder, which, however, are not limitative. In the following formulation examples, "part" or "parts" are by weight.

FORMULATION EXAMPLE 1
Emulsifiable concentrates

| | |
|---|---|
| Compound of the invention | 20 parts |
| Xylene | 55 parts |
| Cyclohexanone | 20 parts |
| Solpol 2680 (trade name, a mixture of a nonionic surface-active agent and an anionic-surface active agent manufactured by Toho Chemical Co., Ltd.) | 5 parts |

The above-mentioned components are homogeneously mixed together to form an emulsifiable concentrate. Upon use, the emulsifiable concentrate is diluted from 50 to 20000 times and applied in an amount of from 0.005 kg/ha to 50 kg/ha in terms of the active ingredient.

FORMULATION EXAMPLE 2
Wettable powder

| | |
|---|---|
| Compound of the invention | 25 parts |
| Zeeklite PFP (trade name, a mixture of kaolinite and sericite manufactured by Zeeklite Mining Industries, Co., Ltd.) | 66 parts |
| Solpol 5039 (trade name, an anionic surface-active agent manufactured by Toho Chemical Co., Ltd.) | 4 parts |
| Carplex #80 (trade name, white carbon manufactured by Shionogi Pharmaceutical Co., Ltd.) | 3 parts |
| Calcium liginin sulfonate | 2 parts |

The above-mentioned components are homogeneously mixed together and ground to form a wettable powder. Upon use, the wettable powder is diluted with from 50 to 20000 times and applied in an amount of from 0.005 kg/ha to 50 kg/ha in terms of the active ingredient.

FORMULATION EXAMPLE 3
Dusts

| | |
|---|---|
| Compound of the invention | 3 parts |
| Carplex #80 (trade name, manufactured by Shionogi Pharmaceutical Co., Ltd.) | 0.5 part |
| Clay | 95 parts |
| Di-isopropyl phosphate | 1.5 parts |

The above-mentioned components are homogeneously mixed together and ground to form a dust. Upon use, the dust is applied in an amount of from 0.005 kg/ha to 50 kg/ha in terms of the active ingredient.

FORMULATION EXAMPLE 4
Granules

| | |
|---|---|
| Compound of the invention | 4 parts |
| Bentonite | 55 parts |
| Talc | 40 parts |
| Calcium lignin sulfonate | 1 part |

The above-mentioned components are mixed homogeneously together and ground, incorporated with a small amount of water and mixed together with stirring. The resulting mixture is granulated by means of extrusion-granulator and dried to form granules. Upon use, the granules are applied in an amount of from 0.005 kg/ha to 50 kg/ha in terms of the active ingredient.

FORMULATION EXAMPLE 5
Flowables

| | |
|---|---|
| Compound of the invention | 25 parts |
| Solpol 3358 (trade name, a nonionic surface-active agent manufactured by Toho Chemical Co., Ltd.) | 10 parts |
| Runox 1000C (trade name, an anionic surface-active agent manufactured by Toho Chemical Co., Ltd.) | 0.5 part |
| 1% aqueous solution of Xanthan gum (natural high-molecular compound) | 20 parts |
| Water | 44.5 parts |

The above-mentioned components except the active ingredient are homogeneously melted, and then the compound of the invention is added thereto and well stirred. The resulting mixture is wet-ground in a sand mill to obtain a flowable. Upon use, the flowable is diluted from 50 to 20000 times and applied in an amount of from 0.005 kg/ha to 50 kg/ha in terms of the active ingredient.

BEST MODE FOR CARRYING THE INVENTION

The present invention is illustrated specifically by referring to the following Examples. However, the present invention is not limited thereto.

Synthesis Example 1
Synthesis of 1,3-dimethyl-5-pyrazolecarboxylic acid (Compound No. 1.1 of the invention)

2.6 g of ethyl 3-methyl-5-pyrazolecarboxylate was reacted with 2 g of dimethyl sulfate at from 160° to 170° C. for 2 hours. To this mixture were added 8.3 g of a 5-N sodium hydroxide solution, and the mixture was reacted at from 80° to 90° C. for 30 minutes. The reaction mixture was air-cooled, and acidified with hydrochloric acid to precipitate crystals. The crystals were collected through filtration, washed with water, and dried to obtain 1.5 g of the Compound No. 1.1 of the present invention.

melting point: from 187° to 189° C.

Synthesis Example 2
Synthesis of 2,4-dimethyl-5-thiazolecarboxylic acid (Compound No. 2.1 of the invention)

Twenty grams of thioacetamide and 40 g of methyl 2-chloroacetoacetate were heat-refluxed in 300 ml of ethanol for 3 hours. The reaction solution was allowed to cool, and 37 g of potassium carbonate were added thereto. The resulting mixture was heat-refluxed again for 3 hours. After the completion of the reaction, ethanol was distilled off, and the residue was extracted with water and with chloroform.

The chloroform layer was dried over anhydrous sodium sulfate, and the solvent was then distilled off under reduced pressure to obtain 41.9 g of ethyl 2,4-dimethyl-5-thiazolecarboxylate.

After 9.7 g of potassium hydroxide were added to 50 ml of methanol and 50 ml of water, 10.2 g of ethyl 2,4-dimethyl-5-thiazolecarboxylate were added dropwise thereto at room temperature. The reaction was conducted at room temperature for 1 hour, and the reaction mixture was then acidified with 2-N hydrochloric acid. After methanol was distilled off, the crystals were collected through filtration, washed with water, and dried to obtain 6.6 g of the Compound No. 2.1 of the present invention.

melting point: from 220° to 225° C.

Synthesis Example 3

Synthesis of ethyl 2-chloro-4-methyl-5-thiazolecarboxylate (Compound No. 2.34 of the invention)

25 g of chlorocarbonylsulphenyl chloride was added dropwise to 25 g of ethyl 3-aminocrotonate in 300 ml of toluene while being cooled with ice. The solution was heat-refluxed for 2 hours, and then cooled. The crystals precipitated were collected through filtration, and then washed twice with toluene to obtain 22.3 g of 4-methyl-5-ethoxycarbonyl-2-thiazolone as purple crystals.

60 ml of phosphorus oxychloride were added to 22.3 g of 4-methyl-5-ethoxycarbonyl-2-thiazolone, and the mixture was heat-refluxed for 16 hours. The reaction solution was cooled, then added to ice water, and neutralized with potassium carbonate. The resulting mixture was extracted with ethyl acetate, and then dried over anhydrous sodium sulfate. The solvent was distilled off under reduced pressure to obtain 19 g of a crude product. This crude product was purified through silica-gel column chromatography (chloroform) to obtain 15.7 g of the Compound No. 2.34 of the present invention as white crystals.

melting point: from 37.5° to 39.0° C.

Synthesis Example 4

Synthesis of ethyl 3-chloro-1-methyl-5-pyrazolecarboxylate (Compound No. 4.3 (a) of the invention)

6.5 g of 3-amino-1-methylpyrazole was dissolved in 55 ml of conc. hydrochloric acid. To this solution was added dropwise a solution of 6.22 g of sodium nitrite in 12.5 ml of water while maintaining the temperature of from 0° to 5° C. through cooling with ice. After the completion of the dropwise addition, the stirring was continued at this temperature for 1 hour. The above-mentioned diazonium solution was added dropwise to a suspension of 7 g of cuprous chloride in 55 ml of chloroform. 2 g of cuprous chloride were twice added thereto during that time.

After the completion of the dropwise addition, the mixture was reacted at 50° C. for 5 hours, and was then stirred at room temperature for 15 hours. This solution was filtered using a Celite, and was then neutralized with a sodium carbonate aqueous solution. The chloroform layer was extracted, and the aqueous layer was further extracted twice with 50 ml of chloroform. The combined chloroform solution was washed with a saturated aqueous solution of sodium chloride, and was dried over anhydrous sodium sulfate. The solvent was distilled off under reduced pressure to obtain 7 g of a crude product.

This crude product was purified through silica-gel column chromatography to obtain 5.2 g of 3-chloro-1-methylpyrazole as a yellow oil.

Then, 5 g of this compound were dissolved in 50 ml of tetrahydrofuran, and the solution was cooled to −70° C. To this solution was added dropwise an LDA solution (prepared from 4.5 g of diisopropylamine and 18.8 g of n-butyl lithium (15%)). After the completion of the dropwise addition, the mixture was further stirred at −70° C. for 1 hour.

The above-mentioned lithiolized pyrazole solution was added dropwise to a solution of 9.5 g of ethyl chloroformate in 50 ml of tetrahydrofuran at −70° C. After the completion of the dropwise addition, the mixture was further stirred at the same temperature for 3 hours. The reaction mixture was quenched with 5-% hydrochloric acid, concentrated under reduced pressure, and extracted twice with 80 ml of chloroform. The organic layer was dried over anhydrous sodium sulfate, and the solvent was then distilled off under reduced pressure to obtain a crude product.

This crude product was purified through silica-gel column chromatography to obtain 7.2 g of the Compound No. 4.3 (a) of the present invention. melting point: from 37.5° to 38.5° C.

Synthesis Example 5

Synthesis of 3-chloro-1-methyl-5-pyrazolecarboxylic acid (Compound No. 4.1 (a) of the invention)

3.5 g of the Compound No. 4.3 (a) formed in Synthesis Example 4 was dissolved in 20 ml of ethanol and 20 ml of water, and 1.8 g of sodium hydroxide were added thereto. The mixture was stirred at room temperature for 15 hours, and was neutralized with hydrochloric acid to precipitate crystals. The crystals were collected through filtration, washed with cold water, and dried to obtain 2.7 g of the Compound No. 4.1 (a) of the present invention.

melting point: from 171° to 174° C.

Synthesis Example 6

Synthesis of 3-chloro-1-methyl-5-pyrazolecarbonyl chloride 100 g of 3-chloro-1-methyl-5-pyrazole-carboxylic acid (the Compound No. 4.1 (a) of the present invention) were suspended in 200 ml of benzene, and 150 ml of thionyl chloride were added thereto dropwise. Then, the mixture was heat-refluxed for 4 hours. The reaction mixture was allowed to cool, and the solvent was then distilled off under reduced pressure. The resulting residue was distilled under reduced pressure to obtain 103 g of the intended 3-chloro-1-methyl-5-pyrazolecarbonyl chloride.

boiling point: from 78° to 80° C./2 mmHg.

Synthesis Example 7

Synthesis of benzyl 3-chloro-1-methyl-5-pyrazolecarboxylate (Compound No. 3.93 (a) of the invention)

1.6 g of benzyl alcohol was dissolved in 50 ml of chloroform. To this solution were added dropwise 1.8 g of triethylamine and then 3.0 g of 3-chloro-1-methyl-5-pyrazolecarbonyl chloride while maintaining the temperature of from 0° to 5° C. through cooling with ice. Further, a small amount of 4-dimethylaminopyridine was added thereto. After the completion of the addition, the mixture was stirred at room temperature for 3.5 hours. To add this solution were added 50 ml of water. The chloroform layer was extracted, and dried over anhydrous sodium sulfate. The solvent was distilled off under reduced pressure, and the resulting residue was purified through silica-gel chromatography (chloroform) to obtain 3.7 g of the compound No. 3.93 (a) of the present invention.

$n_D^{19.9} 1.5564$

The physical data of the compound of the formula [2] which was produced by the above-mentioned methods are shown in Table 7. In this, Compound No. is the same as that shown in Tables 3 to 6.

TABLE 7

| Compound No. | Physical data |
|---|---|
| 3.1 (a) | m.p. 87–88° C. |
| 3.4 (a) | m.p. 52.5–53.5° C. |
| 3.27 (a) | m.p. 83–86° C. |
| 3.29 (a) | m.p. 132.5–133° C. |
| 3.52 (a) | m.p. 165.0–166.0° C. |
| 3.93 (a) | $n_D^{19.9}$ 1.5564 |
| 3.96 (a) | m.p. 96.0–97.0° C. |
| 3.99 (a) | m.p. 31–32° C. |
| 3.105 (a) | m.p. 33.5–35.0° C. |
| 3.108 (a) | m.p. 68.5–69.5° C. |
| 3.109 (a) | m.p. 52–54° C. |
| 3.112 (a) | m.p. 45–46° C. |
| 3.114 (a) | m.p. 76.5–78° C. |
| 3.118 (a) | m.p. 83–84° C. |
| 3.119 (a) | m.p. 91.5–93.0° C. |
| 3.120 (a) | m.p. 60–62° C. |
| 3.121 (a) | m.p. 92–93° C. |
| 3.122 (a) | m.p. 101.0–102.5° C. |
| 3.123 (a) | m.p. 89–90° C. |
| 3.124 (a) | m.p. 131–132° C. |
| 3.125 (a) | m.p. 89–91° C. |
| 3.129 (a) | m.p. 41–43° C. |
| 3.133 (a) | m.p. 96–98° C. |
| 3.136 (a) | m.p. 96–97° C. |
| 3.140 (a) | m.p. 80.5–83.0° C. |
| 3.144 (a) | m.p. 123.0–125.0° C. |
| 3.151 (a) | m.p. 70–71° C. |
| 3.152 (a) | m.p. 44–46° C. |
| 3.154 (a) | m.p. 71.0–72.5° C. |
| 3.155 (a) | m.p. 30–32° C. |
| 3.156 (a) | m.p. 132–136° C. |
| 3.158 (a) | m.p. 40.0–41.5° C. |
| 3.161 (a) | m.p. 77–78° C. |
| 3.163 (a) | $n_D^{20.0}$ 1.5830 |
| 3.166 (a) | m.p. 45–46° C. |
| 3.167 (a) | m.p. 35–36° C. |
| 3.168 (a) | m.p. 96–97° C. |
| 3.170 (a) | $n_D^{20.8}$ 1.5782 |
| 3.178 (a) | m.p. 95–96° C. |
| 3.184 (a) | m.p. 142.0–143.5° C. |
| 3.185 (a) | m.p. 46–48° C. |
| 3.191 (a) | m.p. 32–34° C. |
| 3.198 (a) | m.p. 49–51° C. |
| 3.229 (a) | $n_D^{20.1}$ 1.5459 |
| 3.235 (a) | $n_D^{20.0}$ 1.5306 |
| 3.242 (a) | $n_D^{20.1}$ 1.5570 |
| 3.273 (a) | $n_D^{20.1}$ 1.5439 |
| 3.317 (a) | $n_D^{20.1}$ 1.5444 |
| 3.482 (a) | $n_D^{20.1}$ 1.5323 |
| 3.515 (a) | m.p. 40–42° C. |
| 3.647 (a) | m.p. 72–74° C. |
| 3.650 (a) | m.p. 55–57° C. |
| 3.675 (a) | m.p. 65.5–66.5° C. |
| 4.1 (a) | m.p. 165–168° C. |
| 4.1 (b) | m.p. 119–120° C. |
| 4.1 (f) | m.p. 155–156° C. |
| 4.1 (g) | m.p. 118–122° C. |
| 4.2 (a) | m.p. 23–25° C. |
| 4.3 (a) | m.p. 37.5–38.5° C. |
| 4.4 (a) | $n_D^{20.0}$ 1.4930 |
| 4.5 (a) | $n_D^{20.0}$ 1.3944 |
| 4.6 (a) | $n_D^{20.0}$ 1.4906 |
| 4.8 (a) | $n_D^{20.0}$ 1.4888 |
| 4.10 (a) | $n_D^{19.8}$ 1.4885 |
| 4.13 (a) | $n_D^{20.0}$ 1.4872 |
| 4.14 (a) | m.p. 36–38° C. |
| 4.16 (a) | m.p. 37.5–38.5° C. |
| 4.18 (a) | $n_D^{19.9}$ 1.5099 |
| 4.19 (a) | $n_D^{20.1}$ 1.5054 |
| 4.20 (a) | $n_D^{19.9}$ 1.5140 |
| 4.21 (a) | $n_D^{20.1}$ 1.5119 |
| 4.23 (a) | $n_D^{20.5}$ 1.5104 |
| 4.24 (a) | $n_D^{20.5}$ 1.5082 |
| 4.25 (a) | m.p. 59–62° C. |
| 4.26 (a) | m.p. 83–86° C. |
| 4.27 (a) | oil |
| 4.31 (a) | $n_D^{20.0}$ 1.5092 |

TABLE 7-continued

| Compound No. | Physical data |
|---|---|
| 4.35 (a) | $n_D^{20.0}$ 1.5000 |
| 4.37 (a) | m.p. 35.0–37.5° C. |
| 4.41 (a) | $n_D^{20.1}$ 1.5112 |
| 4.42 (a) | $n_D^{20.1}$ 1.5199 |
| 4.43 (a) | $n_D^{19.7}$ 1.5367 |
| 4.44 (a) | $n_D^{20.1}$ 1.5693 |
| 4.49 (a) | $n_D^{19.9}$ 1.5308 |
| 4.51 (a) | $n_D^{20.2}$ 1.5028 |
| 4.52 (a) | $n_D^{20.0}$ 1.5158 |
| 4.55 (a) | $n_D^{20.1}$ 1.5271 |
| 4.58 (a) | m.p. 50–52° C. |
| 4.59 (a) | m.p. 50–52° C. |
| 4.61 (a) | $n_D^{20.1}$ 1.5236 |
| 4.67 (a) | $n_D^{20.1}$ 1.5057 |
| 4.70 (a) | $n_D^{20.0}$ 1.4743 |
| 4.73 (a) | m.p. 73–74° C. |
| 4.74 (a) | m.p. 49–52° C. |
| 4.75 (a) | $n_D^{20.2}$ 1.5295 |
| 4.76 (a) | $n_D^{19.7}$ 1.5172 |
| 4.77 (a) | $n_D^{19.8}$ 1.4978 |
| 4.78 (a) | $n_D^{19.8}$ 1.5124 |
| 4.82 (a) | m.p. 41–42° C. |
| 4.84 (a) | m.p. 74–76° C. |
| 4.85 (a) | m.p. 60–62° C. |
| 4.86 (a) | m.p. 72–73° C. |
| 4.87 (a) | m.p. 75–76° C. |
| 4.88 (a) | $n_D^{20.1}$ 1.5498 |
| 4.89 (a) | $n_D^{20.1}$ 1.5351 |
| 4.90 (a) | $n_D^{20.1}$ 1.5245 |
| 4.91 (a) | $n_D^{20.1}$ 1.5698 |
| 4.92 (a) | m.p. 65.5–66.5° C. |
| 4.93 (a) | m.p. 88–89° C. |
| 4.94 (a) | m.p. 74–75° C. |
| 4.96 (a) | $n_D^{20.1}$ 1.5161 |
| 4.105 (a) | $n_D^{20.1}$ 1.4975 |
| 4.123 (a) | $n_D^{20.1}$ 1.4924 |
| 4.126 (a) | $n_D^{19.8}$ 1.4972 |
| 4.127 (a) | $n_D^{19.9}$ 1.4920 |
| 4.182 (a) | $n_D^{20.0}$ 1.5412 |
| 4.194 (a) | m.p. 88–91° C. |
| 4.298 (a) | $n_D^{20.0}$ 1.4964 |
| 4.457 (a) | $n_D^{20.1}$ 1.5389 |
| 4.460 (a) | m.p. 47–49° C. |
| 4.490 (a) | m.p. 95.5–96.5° C. |
| 5.7 (a) | viscous substance |
| 5.18 (a) | m.p. 162–163° C. |
| 5.20 (a) | viscous substance |
| 5.22 (a) | m.p. 165–167° C. |
| 5.23 (a) | viscous substance |
| 5.40 (a) | m.p. 51–52.5° C. |
| 5.41 (a) | $n_D^{20.0}$ 1.5002 |
| 6.1 (a) | m.p. 145–146° C. |
| 6.11 (a) | m.p. 156–158° C. |
| 6.25 (a) | m.p. 72–73° C. |
| 6.38 (a) | m.p. 37–44° C. |

The usefulness of the compounds of the present invention is specifically described in the following Test Examples. However, the present invention is not limited thereto.

Test Example 1

Test for effect of controlling Downy mildew (*Pseudoperonospora cubensis*) of a cucumber A chemical solution obtained by diluting the emulsifiable concentrate of the compounds of the present invention to 500 ppm with water was sprayed on a cucumber (brand: Sagami Hanjiro) grown to 1.5-leaf stage in a pot having a diameter of 7 cm at a dose of 20 ml/pot using a spray gun.

The following day, a spore suspension (2 x 105 spores/ml) of a downy mildew strain (*Pseudoperonospora cubensis*) of a cucumber was sprayed to the cucumber, and the pot was placed overnight in an inoculation box having a temperature of 25° C. and a humidity of 95% or more. Then, the pot was put in a greenhouse. After 7 days of inoculation, a ratio of a infected and spotted area formed to the leaf inoculated was measured, and a protective value was calculated according to the following equation.

Protective value =
[1 − (infected and spotted area ratio in treated region/infected and spotted area ratio in untreated region)] × 100

As a result, the following compounds of the present invention indicated a protective value of 100.

Compound No. 1.1, No. 2.1, No. 2.32, No. 3.93 (a), No. 3.99 (a), No. 3.105 (a), No. 3.133 (a), No. 3.158 (a), No. 3.675 (a), No. 4.1 (a), No. 4.1 (g), No. 4.3 (a)

Test Example 2

Test for controlling Rice blast (*Pyricularria oryzae*) of paddy (paddy water application)

10 ml of a chemical solution prepared by diluting the emulsifiable concentrate of the compounds of the present invention 500 ppm with water were drenched to a paddy grown to 1.5-leaf stage in a 1/20000-are beaker pot. After two weeks a conidium suspension of a paddy rice blast strain was inoculated in the thus-treated paddy through spraying. The paddy was infected with the strain at approximately 24° C. and a relative humidity of from 95 to 100% for 24 hours. then, the paddy was left to stand in a greenhouse. After approximately one week, a degree of attack of disease was evaluated according to the six scores of from 0 to 5.

(Evaluation standard)

| Infection index | Degree of attack of disease |
| --- | --- |
| 0 | no attack |
| 1 | lesion number: 1 to 5 |
| 2 | lesion number: 6 to 20 |
| 3 | lesion number: 21 to 40 |
| 4 | lesion number: 41 to 70 |
| 5 | lesion number: 71 or more |

As a result, the following compounds of the present invention indicated an infection index of 1.

Compound No. 1.1, No. 1.3, No. 2.1, No. 2.18, No. 2.32, No. 2.33, No. 2.34, No. 2.41, No. 3.27 (a), No. 3.29 (a), No. 3.93 (a), No. 3.99 (a), No. 3.105 (a), No. 3.122 (a), No. 3.125 (a), No. 3.158 (a), No. 3.185 (a), No. 3.198 (a), No. 3.229 (a), No. 3.242 (a), No. 3.675 (a), No. 4.1 (a), No. 4.3 (a), No. 4.6 (a), No. 4.60 (a), No. 4.61 (a), No. 4.79 (a), No. 4.89 (a), No. 4.83 (a), No. 4.91 (a), No. 4.92 (a), No. 4.94 (a), No. 4.126 (a), No. 4.298 (a), No. 4.460 (a), No. 5.18 (a), No. 5.22 (a), No. 6.38 (a), No. 4.1 (g)

Test Example 3

Test for controlling Rice blast (*Pyricularria oryzae*) of paddy (application of granules)

An aquatic rice (brand: Nihonbare) was grown to 3- to 4-leaf stage in a 1/10000-are pot under submerged culture, and the water surface of this pot was treated with granule containing 4% of an active compound. After two weeks of treatment, a conidium suspension of a paddy rice blast strain was inoculated in the thus-treated paddy rice through spraying. The pot was retained at approximately 24° C. and a relative humidity of from 95 to 100% for 24 hours. Then, this pot was moved to a greenhouse. After 7 days of inoculation, the degree of attack of disease was evaluated according to the same six scores as in Test Example 2.

The results are shown below.

| Invention Compound | Amount of an active ingredient (g/m²) | Infection index |
| --- | --- | --- |
| No. 1.1 | 0.24 | 1 |
| No. 2.1 | 0.24 | 1 |
| No. 2.32 | 0.24 | 1 |
| No. 4.1 (a) | 0.24 | 1 |
| No. 4.3 (a) | 0.24 | 1 |
| untreated lot | — | 5 |

Test Example 4

Test for controlling Rice blast (*Pyricularria oryzae*) of paddy (seedling box treatment)

An aquatic rice (brand: Nihonbare) was cultivated for 25 days using a seedling culture box (30 cm×60 cm×3 cm), and was treated with a dust containing 4% of an active compound. The following day, a young seedling was transplanted into a 1/10000-are pot, and was grown under submerged culture for 3 weeks. Thereafter, the inoculation and the evaluation were conducted in the same manner as in Test Example 3.

The results are shown below.

| Invention Compound | Amount of an active ingredient (g/box) | Infection index |
| --- | --- | --- |
| No. 1.1 | 2.4 | 1 |
| No. 2.1 | 2.4 | 1 |
| No. 2.32 | 2.4 | 1 |
| No. 4.1 (a) | 2.4 | 1 |
| No. 4.3 (a) | 2.4 | 1 |
| untreated lot | — | 5 |

INDUSTRIAL AVAILABILITY

The plant disease control agent of the present invention, the compound of the present invention and the plant disease control agent containing said compound exhibit an excellent agricultural and horticultural activity of controlling diseases, and do not damage useful crops. Accordingly, it is useful as an agricultural and horticultural microbicide.

We claim:

1. Pyrazolecarboxylic acid derivative of the formula [2]:

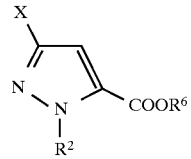

[2]

wherein

X represents a halogen atom, $R^2$ represents a $C_1$–$C_4$ alkyl group, $R^6$ represents a hydrogen atom, an alkali metal atom, an alkaline-earth metal atom, ammonium, sulfonium, phosphonium, an optionally substituted aryl group, an optionally substituted heteroaryl group, an optionally substituted heterocyclyl group, an optionally substituted aryl $C_2$–$C_4$ alkenyl group, —[C($R^7$)($R^8$)]$_m$—$R^9$, —N($R^{10}$)($R^{11}$) or —N=C($R^{12}$)($R^{13}$), $R^7$ and $R^8$, independently from each other, represent a hydrogen atom, a halogen atom, a $C_1$–$C_6$ alkyl group ($R^7$ and $R^8$ may together form a cyclic alkyl group), a $C_2$–$C_6$ alkenyl group, a $C_2$–$C_6$ alkynyl group, a $C_1$–$C_6$ haloalkyl group, an optionally substituted aryl group, an optionally substituted heteroaryl group, a $C_1$–$C_4$ alkylcarbonyl group, a $C_1$–$C_6$ alkoxycarbonyl group or a cyano group, m is 0 or 1 to 5, $R^9$ represents a hydrogen atom, a halogen atom, a $C_1$–$C_{10}$ alkyl group, a $C_2$–$C_{10}$ alkenyl group, a $C_2$–$C_{10}$ alkynyl group, a $C_1$–$C_{10}$ haloalkyl group, a $C_2$–$C_{10}$ haloalkenyl group, a $C_3$–$C_{10}$ cycloalkyl group, an optionally substituted aryl group, an optionally substituted heteroaryl group, an optionally substituted heterocyclyl group, a $C_1$–$C_6$ alkoxy group, a $C_1$–$C_5$ haloalkoxy group, a $C_2$–$C_6$ alkenyloxy group, a $C_2$–$C_6$ haloalkenyloxy group, a $C_2$–$C_6$ alkynyloxy group, a $C_3$–$C_8$ cycloalkyloxy group, a $C_1$–$C_6$ alkoxy $C_1$–$C_6$ alkyl group, an optionally substituted arylalkyloxy group, an optionally substituted aryloxy group, an optionally substituted heteroaryloxy group, a cyano group, —C(O)—$R^{14}$, —S(O)$_n$$R^{15}$, —N($R^{16}$)($R^{17}$), —ON=C($R^{18}$)($R^{19}$) or OH, $R^{10}$ and $R^{11}$, independently from each other, represent a hydrogen atom, a $C_1$–$C_6$ alkyl group, a $C_1$–$C_6$ haloalkyl group, a $C_2$–$C_6$ alkenyl group, a $C_2$–$C_6$ haloalkenyl group, a $C_2$–$C_6$ alkynyl group, a $C_1$–$C_4$ alkoxy $C_1$–$C_4$ alkyl group, a $C_1$–$C_4$ alkylthio $C_1$–$C_4$ alkyl group, a $C_1$–$C_6$ alkylcarbonyl group, a $C_1$–$C_6$ alkoxycarbonyl group, a $C_1$–$C_6$ alkylsulfonyl group, an optionally substituted aryl group, an optionally substituted arylcarbonyl group or an optionally substituted arylsulfonyl group, $R^{12}$ represents a $C_1$–$C_6$ alkyl group, a $C_1$–$C_6$ haloalkyl group or an optionally substituted aryl group, $R^{13}$ represents an amino group, a $C_1$–$C_5$ monoalkylamino group or a $C_1$–$C_5$ dialkylamino group, $R^{14}$ represents a hydrogen atom, OH group, a $C_1$–$C_6$ alkyl group, a $C_1$–$C_6$ haloalkyl group, an optionally substituted aryl group, a $C_1$–$C_6$ alkoxy group, a $C_1$–$C_6$ haloalkoxy group, a $C_2$–$C_6$ alkenyloxy group, a $C_2$–$C_6$ haloalkenyloxy group, a $C_2$–$C_6$ alkynyloxy group or an optionally substituted heterocyclyloxy group, n is 0, 1 or 2, $R^{15}$ represents a hydrogen atom, a $C_1$–$C_6$ alkyl group, a $C_1$–$C_6$ haloalkyl group or a $C_2$–$C_6$ alkenyl group, $R^{16}$ and $R^{17}$, independently from each other, represent a hydrogen atom, a $C_1$–$C_6$ alkyl group ($R^{16}$ and $R^{17}$ may together form a cyclic alkyl group), a $C_3$–$C_6$ cycloalkyl group, an optionally substituted aryl group, an optionally substituted aryl $C_2$–$C_4$ alkyl group, a $C_1$–$C_6$ alkylcarbonyl group, an optionally substituted arylcarbonyl group or a $C_1$–$C_6$ alkoxycarbonyl group, $R^{18}$ and $R^{19}$, independently from each other, represent a hydrogen atom, a $C_1$–$C_6$ alkyl group or an optionally substituted aryl group, the expression "optionally substituted" means unsubstituted or substituted with from 1 to 9 groups selected from a halogen atom, a cyano group, a nitro group, a $C_1$–$C_4$ alkyl group, a $C_1$–$C_4$ alkoxy group, a $C_1$–$C_4$ haloalkyl group, a $C_1$–$C_4$ haloalkoxy group, an aryl group, an aryloxy group, a benzyl group, a benzyloxy group, a $C_3$–$C_6$ cycloalkyl group, a $C_1$–$C_4$ alkoxycarbonyl group, a $C_1$–$C_4$ alkylthio group, a $C_1$–$C_4$ alkylsulfinyl, a $C_1$–$C_4$ alkylsulfonyl group, a styryl group, an amino group, a $C_1$–$C_4$ alkoxycarbonylamino group, a $C_1$–$C_4$ alkoxycarbonyloxy group and/or an aminocarbonyl group, the "aryl" group means a residue obtained by removing one hydrogen atom bound to a carbon atom of an aromatic ring from an aromatic hydrocarbon compound, the "heteroaryl" group means a residue obtained by removing one hydrogen atom bound to a carbon atom of a heterocyclic ring from a 5-membered or 6-membered aromatic heterocyclic compound, and the "heterocyclyl group" means a residue obtained by removing a hydrogen atom bound to a carbon atom of a heterocyclic ring from a 3- to 6-membered non-aromatic heterocyclic compound.

2. Pyrazolecarboxylic acid derivatives as claimed in claim 1, wherein X represents a chlorine atom or a bromine atom, and $R^2$ is a methyl group.

3. Pyrazolecarboxylic acid derivatives as claimed in claim 1, wherein X represents a chlorine atom or a bromine atom, $R^2$ is a methyl group, and $R^6$ represents —[C($R^7$)($R^8$)]$_m$— $R^9$ (wherein $R^7$, $R^8$, $R^9$ and m have the same meanings as defined above).

4. Pyrazolecarboxylic acid derivatives as claimed in claim 3, wherein X represents a chlorine atom, $R^2$ represents a methyl group, $R^7$ and $R^8$ represent, independently from each other, a hydrogen atom, a methyl group or an ethyl group, $R^9$ is a hydrogen atom, a $C_1$–$C_{10}$ alkyl group or an optionally substituted aryl group, and m is 0, 1 or 2.

5. Pyrazolecarboxylic acid derivatives as claimed in claim 1, wherein X represents a chlorine atom, $R^2$ represents a methyl group, and $R^6$ represents a methyl group, an ethyl group, a propyl group, a butyl group, a phenyl group, a benzyl group, a 2phenylethyl group a 2-phenylpropyl group.

6. Plant disease control agent containing as active ingredientone or more pyrazolecarboxylic acid derivatives as claimed in claim 1, 2, 3, 4 or 5.

7. A plant disease described in claim 6 is Rice blast (*Pyricularia oryzae*) of paddy.

\* \* \* \* \*